United States Patent
Wakefield et al.

(10) Patent No.: US 9,474,804 B2
(45) Date of Patent: *Oct. 25, 2016

(54) POLY(VINYL ESTER) POLYMERS FOR IN VIVO NUCLEIC ACID DELIVERY

(71) Applicant: Arrowhead Madison Inc., Madison, WI (US)

(72) Inventors: Darren H Wakefield, Fitchburg, WI (US); Nicholas A Rossi, Madison, WI (US); Dan Sheik, San Diego, CA (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/746,070

(22) Filed: Jun. 22, 2015

(65) Prior Publication Data

US 2015/0283256 A1 Oct. 8, 2015

Related U.S. Application Data

(63) Continuation of application No. 14/561,339, filed on Dec. 5, 2014, now Pat. No. 9,089,611, which is a continuation of application No. 13/592,393, filed on Aug. 23, 2012, now Pat. No. 8,932,572.

(60) Provisional application No. 61/527,703, filed on Aug. 26, 2011.

(51) Int. Cl.
*A61K 47/48* (2006.01)
*C08F 218/04* (2006.01)
(Continued)

(52) U.S. Cl.
CPC ..... *A61K 47/48176* (2013.01); *A61K 31/7105* (2013.01); *A61K 47/482* (2013.01);
(Continued)

(58) Field of Classification Search
CPC .......... A61K 47/482; A61K 7/48176; A61K 31/7105; C08F 218/04; C08F 218/10; C12N 15/113
USPC ....................... 424/78.29; 525/54.2; 526/301
See application file for complete search history.

(56) References Cited

U.S. PATENT DOCUMENTS

| 5,885,968 A | 3/1999 | Biessen et al. |
| 6,291,620 B1 | 9/2001 | Moad et al. |

(Continued)

FOREIGN PATENT DOCUMENTS

| WO | 95/04026 A1 | 2/1995 |
| WO | 98/01478 A1 | 1/1998 |

(Continued)

OTHER PUBLICATIONS

Amarzguioui et al. "An algorithm for selection of functional siRNA sequences" Biochemical and Biophysical Research Communications 2004 vol. 316, p. 1050-1058.

(Continued)

*Primary Examiner* — Blessing M Fubara

(57) ABSTRACT

The present invention is directed membrane active poly (vinyl ester) polymers and compositions for targeted delivery of RNA interference (RNAi) polynucleotides to cells in vivo. RNAi polynucleotides are conjugated to the poly(vinyl ester) polymers and the polymers are reversibly modified to enable in vivo targeted delivery. Membrane activity of the poly(vinyl ester) provides for movement of the RNAi polynucleotides from outside the cell to inside the cell. Reversible modification provides physiological responsiveness.

30 Claims, 5 Drawing Sheets amphipathic poly(vinyl ester) random copolymer

(51) Int. Cl.
C08F 218/10 (2006.01)
C12N 15/113 (2010.01)
A61K 31/7105 (2006.01)

(52) U.S. Cl.
CPC .......... C08F218/04 (2013.01); C08F 218/10 (2013.01); C12N 15/113 (2013.01); *C08F 2218/22* (2013.01); *C12N 2310/14* (2013.01); *C12N 2310/351* (2013.01); *C12N 2320/30* (2013.01)

(56) References Cited

U.S. PATENT DOCUMENTS

| | | | |
|---|---|---|---|
| 6,376,626 B1 | 4/2002 | Chiefari et al. | |
| 6,642,318 B1 | 11/2003 | Chiefari et al. | |
| 6,747,111 B2 | 6/2004 | Chiefari et al. | |
| 8,932,572 B2* | 1/2015 | Wakefield | A61K 47/482 424/78.17 |
| 9,089,611 B2* | 7/2015 | Wakefield | A61K 47/482 |
| 2004/0162260 A1 | 8/2004 | Rozema et al. | |
| 2008/0152661 A1 | 6/2008 | Rozema et al. | |
| 2009/0048410 A1 | 2/2009 | Wakefield et al. | |
| 2011/0009571 A1* | 1/2011 | Taft | A61K 9/0019 525/450 |
| 2011/0143434 A1 | 6/2011 | Stayton | |
| 2011/0207799 A1 | 8/2011 | Rozema et al. | |
| 2011/0224377 A1 | 9/2011 | Mahanthappa et al. | |
| 2011/0286957 A1 | 11/2011 | Prieve | |

FOREIGN PATENT DOCUMENTS

| | | |
|---|---|---|
| WO | 99/05099 A1 | 2/1999 |
| WO | 99/31144 A1 | 6/1999 |
| WO | 2008/022309 A2 | 2/2008 |
| WO | 2010/083569 A1 | 7/2010 |
| WO | 2011/112911 A2 | 9/2011 |
| WO | 2011/115641 A1 | 9/2011 |
| WO | 2011/163121 A1 | 12/2011 |

OTHER PUBLICATIONS

Baenziger Ju et al. "Galactose and N-acetylgalactosamine-specific endocytosis of glycopeptides by isolated rat hepatocytes" Cell (1980) 22(2): 611-620.
Biessen et al. "Synthesis of Cluster Galactosides with High Affinity for the Hepatic Asialoglycoprotein Receptor" Journal of Medicinal Chemistry (1995) 38(9): 1538-1546.
Chalk et al. "Improved and automated prediction of effective siRNA" Biochemical and Biophysical Research Communications 2004 vol. 319, p. 264-274.
Connolly et al. "Binding and endocytosis of cluster glycosides by rabbit hepatocytes. Evidence for a short-circuit pathway that does not lead to degradation" Journal of Biological Chemistry (1982) 257(2): 939-945.
Frier et al. "Improved free-energy parameters for predictions of RNA duplex stability" Proceedings from the National Academy of Sciences USA 1986 vol. 83, p. 9373-9377.
Heale et al. "siRNA target site secondary structure predictions using local stable substructures" Nucleic Acids Research (2005) 33(3), p.
Iobst St et al. "Selective Sugar Binding to the Carbohydrate Recognition Domains of the Rat Hepatic and Macrophage Asialoglycoprotein Receptors." Journal of Biological Chemistry (1996) 271(12), p. 6686-6693.
Khvorova et al. "Functional siRNAs and miRNAs Exhibit Strand Bias" Cell 2003 vol. 115, p. 209-216.
Rozema DB et al. "Endosomolysis by Masking of a Membrane-Active Agent (EMMA) for Cytoplasmic Release of Macromolecules" Bioconjugate Chemistry (2003) 14(1): 51-57.
Schwarz et al. "Asymmetry in the Assembly of the RNAi Enzyme Complex" Cell 2003 vol. 115, p. 199-208.
Sumerlin BS et al. "Block copolymerization of vinyl ester monomers via RAFT/MADIX under microwave irradiation" Polymer (2011), vol. 52, No. 14, p. 3038-3045.
Turner et al. "Free Energy Increments for Hydrogen Bonds in Nucleic Acid Base Pairs" Journal of the American Chemical Society 1987 vol. 209, p. 3783-3785.
Ui-Tei et al. "Guidelines for the selection of highly effective siRNA sequences for mammalian and chick RNA interference" Nucleic Acids Research 2004 vol. 32(3)936-948.
Xu FJ, Yang WT "Polymer vectors via controlled/living radical polymerization for gene delivery" Progress in Polymer Science 2011, vol. 36, p. 1099-1131.
Wincott F et al. "Synthesis, deprotection, analysis and purification of RNA and ribozymes" Nucleic Acids Research (1995) 23(14): 2677-2684.
Wolfert MA, Dash PR, Nazarpva O, Oupicky D, Seymour LW, Smart S, Strohalm J, Ulbrich K. "Polyelectrolyte vectors for gene delivery: influence of cationic polymer on biophysical properties of complexes formed with DNA" Bioconjugate Chem. 1999, vol. 10, p. 993-1004.
Ahmed M, Bhuchar N, Ishihara K, Narain R. "Well-controlled cationic water-soluble phospholipid polymer-DNA nanocomplexes for gene delivery." Bioconjugate Chem. 2011, vol. 22, p. 1228-1238.
Boyer C, Bulmus V, Davis TP, Ladmiral V, Liu J, Perrier S "Bioapplications of RAFT Polymerization" Chem. Rev. 2009 vol. 109, No. 11, p. 5402-5436.
Chiefari J et al. "Living Free-Radical Polymerization by Reversible Addition-Fragmentation Chain Transfer: The RAFT Process" Macromolecules (1998), vol. 31, No. 16, p. 5559-5562.
Chu DS et al. "Application of Living Free Radical Polymerization for Nucleic Acid Delivery" Accounts of Chemical Research 2012 vol. 45, No. 7, p. 1089-1099.
Convertine AJ et al. "Development of a novel endosomolytic diblock copolymer for siRNA delivery" Journal of Controlled Release (2009) vol. 133, p. 221-229.
De Smedt SC, Demeester J, Hennink WE. "Cationic polymer based gene delivery systems" Pharm. Res. 2000, vol. 17, p. 113-126.
Duvall CL et al. "Intracellular Delivery of a Proapoptotic Peptide via Conjugation to a RAFT Synthesized Endosomolytic Polymer" Molecular Pharmaceutics (2009).
Kuroda K et al. "The Role of Hydrophobicity in the Antimicrobial and Hemolytic Activities of Polymethacrylate Derivatives" Chem. Eur. J. (2009) vol. 15, p. 1123-1133.
Lee SB, Russell AJ, Matyjaszewski, K. ATRP synthesis of amphiphilic random, gradient, and block copolymers of 2-(dimethylamino)ethyl methacrylate and n-butyl methacrylate in aqueous media, Biomacromolecules (2003) vol. 4, No. 5, p. 1386-1393.
Lipscomb CE, Mahanthappa, MK. "Poly(vinyl ester) Block Copolymers Synthesized by Reversible Addition-Fragmentation Chain Transfer Polymerizations" Macromolecules (2009), vol. 42. No. 13, p. 4571-4579.
Liu Y et al. "Bionanoparticles of amphiphilic copolymers polyacrylate bearing cholesterol and ascorbate for drug delivery" Journal of Colloid and Interface Science (2012), vol. 377, No. 1, p. 197-206.
Lowe AB, McCormick CL. "Homogeneous Controlled Free Radical Polymerization in Aqueous Media" Australian Journal of Chemistry (2002), vol. 55, p. 367-379.
Moad G et al "Living Radical Polymerization by the RAFT Process—A Second Update." Aust. J. Chem. 2009, vol. 62, p. 1402-1472.
Moad G, Rizzardo E, Thang SH. "Toward Living Radical Polymerization." Acc. Chem. Res. 2008, vol. 41, p. 1133-1142.
Vidyasagar Malepu et al. "RAFT Polymerization of Vinyl Acetate, Styrene and Acrylates Using N,N-Dithiocarbamates" in Controlled/Living Radical Polymerization: Progress in RAFT, DT, NMP & OMRP, Matyjaszewski K, editor; ACS Symposium Series, vol. 1024, chapter 3, pp. 37-47; American Chemical Society, Washington D.C., 2009.
Office Action for corresponding China application 201280041442.
European Search Opinion for corresponding application EP12827106.

(56) References Cited

OTHER PUBLICATIONS

International Search Report for corresponding application PCT/US 12/51968.

Mahanthappa et al.; "Poly(vinyl ester) Block Copolymers Synthesized by Reversible Addition-Fragmentation Chain Transfer Polymerizations"; (2009); Macromoleccules; vol. 42; pp. 4571-4579.

* cited by examiner amphipathic poly(vinyl ester) random copolymer

A.

NAG-AlaCit-PABC-PNP

B.

NAG-GluGly-PABC-PNP

C.

NAG-PEG4-PheCit-PABC-PNP

D.

NAG-PEG7-PheCit-PABC-PNP

E.

PEG-GlyGly-PABC-PNP

F.

PEG-AsnGly-PABC-PNP

G.

PEG-PheLys-PABC-PNP

H.

PEG-ValCit-PABC-PNP

I.

PEG-AlaAsn-PABC-PNP

J.

PEG-PheLys(CH₃)₂-PABC-PNP

K.

PEG₁₂-Phe-Cit-PABC-PNP

POLY(VINYL ESTER) POLYMERS FOR IN VIVO NUCLEIC ACID DELIVERY

CROSS-REFERENCE TO RELATED APPLICATIONS

This application is a continuation of U.S. application Ser. No. 14/561,339, filed 5 Dec. 2014, which is a continuation of U.S. application Ser. No. 13/923,393 filed 23 Aug. 2012, now U.S. Pat. No. 8,932,572, which claims the benefit of U.S. Provisional Application No. 61/527,703 filed 26 Aug. 2011.

BACKGROUND OF THE INVENTION

The delivery of polynucleotides and other substantially cell membrane impermeable compounds into a living cell is highly restricted by the complex membrane system of the cell. Drugs used in antisense, RNAi, and gene therapies are relatively large hydrophilic polymers and are frequently highly negatively charged. Both of these physical characteristics preclude their direct diffusion across the cell membrane. For this reason, the major barrier to polynucleotide delivery is the delivery of the polynucleotide across a cell membrane to the cell cytoplasm or nucleus.

One means that has been used to deliver small nucleic acid in vivo has been to attach the nucleic acid to either a small targeting molecule or a lipid or sterol. While some delivery and activity has been observed with these conjugates, the nucleic acid dose required with these methods has been prohibitively large for practical application.

Numerous transfection reagents have been developed that achieve reasonably efficient delivery of polynucleotides to cells in vitro. However, in vivo delivery of polynucleotides using these same transfection reagents is complicated and rendered ineffective by in vivo toxicity, serum interactions, and poor targeting. Transfection reagents that work well in vitro, cationic polymers and lipids, typically form large electrostatic particles and destabilize cell membranes. The positive charge of in vitro transfection reagents facilitates association with nucleic acid via charge-charge (electrostatic) interactions thus forming the nucleic acid/transfection reagent complex. Positive charge is also beneficial for nonspecific binding of the vehicle to the cell and for membrane fusion, destabilization, or disruption. Destabilization of membranes facilitates delivery of the substantially cell membrane impermeable polynucleotide across a cell membrane. While these properties facilitate nucleic acid transfer in vitro, they cause toxicity and ineffective targeting in vivo. Cationic charge results in interaction with serum components, which causes destabilization of the polynucleotide-transfection reagent interaction and poor bioavailability and targeting. Membrane activity of transfection reagents, which can be effective in vitro, often leads to toxicity in vivo.

For in vivo delivery, the vehicle (nucleic acid and associated delivery agent) should be small, less than 100 nm in diameter, and preferably less than 50 nm. Even smaller complexes, less than 20 nm or less than 10 nm would be more useful yet. Delivery vehicles larger than 100 nm have very little access to cells other than blood vessel cells in vivo. Complexes formed by electrostatic interactions tend to aggregate or fall apart when exposed to physiological salt concentrations or serum components. Further, cationic charge on in vivo delivery vehicles leads to adverse serum interactions and therefore poor bioavailability. Interestingly, high negative charge can also inhibit in vivo delivery by interfering with interactions necessary for targeting. Thus, near neutral vehicles are desired for in vivo distribution and targeting. Without careful regulation, membrane disruption or destabilization activities are toxic when used in vivo. Balancing vehicle toxicity with nucleic acid delivery is more easily attained in vitro than in vivo.

Rozema et al., in U.S. Patent Publication 20040162260 demonstrated a means to reversibly regulate membrane disruptive activity of a membrane active polyamine by reversible conversion of primary amines to pairs of carboxyl groups ($\beta$ carboxyl and $\gamma$ carboxyl of 2-propionic-3-methylmaleic anhydride). Rozema et al. (Bioconjugate Chem. 2003, 14, 51-57) reported that the $\beta$ carboxyl did not exhibit a full apparent negative charge and by itself was not able to inhibit membrane activity. The addition of the $\gamma$ carboxyl group was reported to be necessary for effective membrane activity inhibition. However, because the vehicle was highly negatively charged, with both the nucleic acid and the modified polymer having high negative charge density, this system was not efficient for in vivo delivery.

By substituting neutral hydrophilic targeting (galactose) and steric stabilizing (PEG) groups for the $\gamma$ carboxyl of 2-propionic-3-methylmaleic anhydride, Rozema et al. were able to retain overall water solubility and reversible inhibition of membrane activity while incorporating effective in vivo hepatocyte cell targeting (U.S. Patent Publication 20080152661).

We now describe new membrane active polymers and compositions made with the described polymers for use in delivery of nucleic acids to cells in vivo. These new polymers provide improved therapeutic potential over those previously described.

SUMMARY OF THE INVENTION

In a preferred embodiment, the invention features amphipathic cationic poly(vinyl ester) random copolymers particularly suited for delivering polynucleotides to cells in vivo. An amphipathic cationic poly(vinyl ester) random copolymer of the invention comprises a plurality of amine-containing vinyl ester monomers and a plurality of first hydrophobic vinyl ester monomers. The amine-containing monomers contain pendant primary amine groups. The hydrophobic monomers contain pendent hydrophobic groups having 2-20 carbon atoms selected from the group consisting of: hydrocarbon group, alkyl group, alkenyl group, alkynyl group, alkoxy alkyl group, aromatic group, and aryl group. The polymers may further comprise a plurality of second amine-containing vinyl ester monomers or a plurality of second hydrophobic vinyl ester monomers. Second amine-containing vinyl ester monomers contain pendant amine groups selected from the group consisting of: primary amine, secondary amine, tertiary amine, quaternary amine, protected amine, nitrogen heterocycle, aldimine, hydrazide, hydrazone, and imidazole. In addition to being amphipathic, the poly(vinyl ester) random copolymers of the invention are membrane active. A preferred poly(vinyl ester) random copolymer comprises primary amine containing and butyryl vinyl ester monomers.

Poly(vinyl ester) random copolymers of the invention may be synthesized from two, three, or four different monomers. Monomers may be selected from the list comprising: protected amine vinyl ester, imidazole vinyl ester, alkyl vinyl ester, alkenyl vinyl ester, alkynyl vinyl ester, aromatic vinyl ester, and aryl vinyl ester. Protected amine vinyl ester monomers include, but are not limited to: tert-Butoxycabonyl (Boc) protected amine containing vinyl ester. Protected primary amine monomers are copolymerized with alkyl vinyl ester monomers. The amine protecting groups are then removed post-polymerization to form aqueous soluble, amphipathic random copolymers. The aliphatic hydrophobic groups may be linear, branched, or cyclic and may contain one or more substitutions of heteroatoms.

In a preferred embodiment, poly(vinyl ester) random copolymers are synthesized by Reversible Addition-Fragmentation chain Transfer (RAFT) polymerization. In one embodiment, the RAFT polymerization is carried out using Malonate N,N-diphenyl dithiocarbamate (MDP-DTC). Using RAFT polymerization, and optionally fractionization, polymers having a polydispersity of less than 1.5, or more preferably less than 1.4 or 1.3, are possible.

For delivery of a polynucleotide to a cell in vivo, the described amphipathic poly(vinyl ester) random copolymers are reversibly modified. Reversible modification comprises attachment of a plurality of masking agents, as defined herein, to polymer primary amines through a plurality of reversible physiologically labile covalent bonds. Reversible physiologically labile covalent bonds may be selected from the group comprising: pH labile bonds and enzymatically cleavable bonds. As used herein, reversible modification means polymer primary amines are restored upon cleavage of the physiologically labile covalent bond linking the masking agent to the polymer. In a preferred embodiment, more than 50%, more than 60%, more than 70%, more than 80%, or more than 90% of polymer primary amines are modified by reversible attachment of masking agents. Masking agents may be selected from the group comprising: steric stabilizers and targeting groups. The masking agents improve biodistribution or targeting of the polymer or a polymer-polynucleotide conjugate in vivo. Masking agents may inhibit non-specific interactions of the polymer with serum components or non-target cells. Masking agents may reduce aggregation of the polymer or polymer-polynucleotide conjugate. Masking agents containing targeting groups enhance cell-specific targeting or cell internalization by targeting the conjugate system to a cell surface receptor. The masking agents can be conjugated to the polymer prior to or subsequent to conjugation of the polymer to a polynucleotide.

In another preferred embodiment, a polynucleotide is linked to the polymer of the invention through a second physiologically labile covalent bond. One or more polynucleotides may be linked to the polymer via the second physiologically labile covalent bonds. The labile bond linking the masking agent to the polymer, first labile bond, and the labile bond linking the polynucleotide to the polymer, second labile bond, maybe cleaved under the same or similar conditions or they may be cleaved under distinct conditions, i.e. they may be orthogonal labile bonds. The polynucleotide may be selected from the group comprising: DNA, RNA, blocking polynucleotide, oligonucleotide, RNA interference polynucleotide, siRNA, microRNA, mRNA, and shRNA. Second physiologically labile covalent bonds may be selected from the group comprising: pH labile bonds, enzymatically cleavable bonds, disulfide bonds, and nucleic acid ester bonds.

In a preferred embodiment, we describe a composition comprising: an amphipathic poly(vinyl ester) random copolymer covalently linked to: a) one or more targeting groups and or steric stabilizers via reversible physiologically labile covalent bonds; and, b) one or more polynucleotides via orthogonal second physiologically labile covalent bonds. The polynucleotide-polymer conjugate is administered to a mammal in a pharmaceutically acceptable carrier or diluent.

In a preferred embodiment, we describe a polymer conjugate system for delivering a membrane impermeable molecule to a cell and releasing the molecule in the cell. The polymer conjugate system comprises the membrane impermeable molecule reversibly linked to a reversibly modified poly(vinyl ester) of the invention. A preferred membrane impermeable molecule comprises a polynucleotide. A preferred polynucleotide comprises an RNA interference polynucleotide. A preferred RNA interference polynucleotide comprises an siRNA or miRNA. The polymer or polynucleotide-polymer conjugate is administered to a mammal in a pharmaceutically acceptable carrier or diluent.

In another preferred embodiment, the invention features a composition for delivering an RNA interference polynucleotide to a liver cell in vivo comprising: an amphipathic poly(vinyl ester) random copolymer covalently linked to: one or more targeting groups and/or steric stabilizers via reversible physiologically labile covalent bonds and an RNA interference polynucleotide conjugated to a polynucleotide targeting group (polynucleotide conjugate). A preferred polynucleotide targeting group is a hydrophobic group containing at least 20 carbon atoms. Another preferred polynucleotide targeting group is a trivalent galactosamine. The poly(vinyl ester) and the polynucleotide-conjugate are synthesized separately and may be supplied in separate containers or a single container. In this composition, the polynucleotide is not conjugated to the polymer. The modified polymer and polynucleotide-conjugate are administered to a mammal in pharmaceutically acceptable carriers or diluents. In one embodiment, the delivery polymer and the RNAi polynucleotide conjugate may be combined in a solution prior to administration to the mammal. In another embodiment, the delivery polymer and the RNAi polynucleotide conjugate may be co-administered to the mammal in separate solutions. In yet another embodiment, the delivery polymer and the RNAi polynucleotide conjugate may be administered to the mammal sequentially. For sequential administration, the delivery polymer may be administered prior to administration of the RNAi polynucleotide conjugate. Alternatively, for sequential administration, the RNAi polynucleotide conjugate may be administered prior to administration of the delivery polymer.

In another embodiment, the described amphipathic poly (vinyl ester) random copolymers are suitable for delivering polynucleotides to mammalian cells in vitro. For in vitro cell delivery, the amphipathic poly(vinyl ester) random copolymers may be reversibly modified as described or used without reversible modification. They may also be combined with lipids or other polymers.

DETAILED DESCRIPTION OF THE INVENTION

Figure 1:
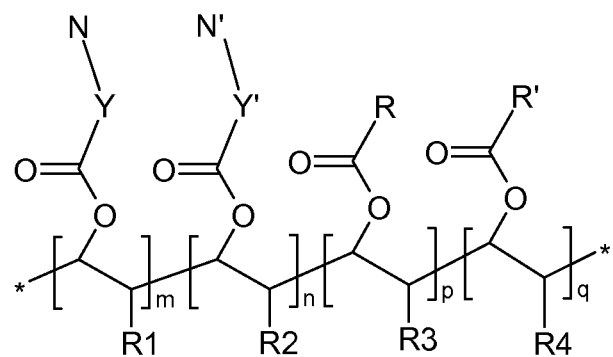
FIG. 1. Illustration shown the structure of an various amphipathic poly(vinyl ester) random copolymer wherein:
N is a primary amine having the form —$NH_2$,
N' is a secondary, tertiary, or quaternary amine having the form —$NR^5H$, —$NR^5R^6$, or —$NR^5R^6R^7$ (wherein $R^5$, $R^6$, and $R^7$ are independently selected from —$CH_3$ and —$CH_2$—$CH_3$,) or alternatively N' can be a nitrogen heterocycle, aldimine, hydrazide, hydrazone, or imidazole,
Y and Y' are linker groups,
R and R' are hydrophobic groups independently having 2-20 carbon atoms,
R1, R2, R3, and R4 are independently selected from hydrogen (—H) and methyl (—$CH_3$),
m and p are integers greater than zero (0), n and q are integers greater than or equal to zero (0), and the ratio (m+n)/(p+q) is 1-9.

The present invention relates to amphipathic poly(vinyl ester) random copolymers and conjugate systems thereof useful for the delivery of biologically active substances, such as nucleic acids, peptides, and proteins. The delivery of nucleic acids and other substantially cell membrane impermeable compounds into a living cell is highly restricted by the complex membrane system of the cell. For in vivo delivery the amphipathic poly(vinyl ester) random copolymers are reversibly modified by covalent attachment of masking agents via physiologically labile linkages.

In one embodiment, the present invention is directed to membrane active poly(vinyl ester) random copolymers of formula (I):

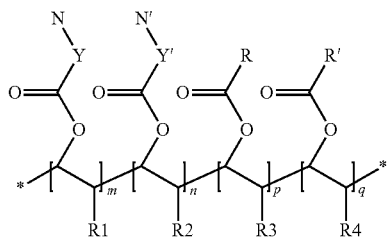

wherein:

N is a primary amine having the form —NH$_2$,

N' is a secondary, tertiary, or quaternary amine having the form —NR$^5$H, —NR$^5$R$^6$, or —NR$^5$R$^6$R$^7$ wherein R$^5$, R$^6$, and R$^7$ are independently selected from —CH$_3$ and —CH$_2$—CH$_3$, or alternatively N' can be a nitrogen heterocycle, aldimine, hydrazide, hydrazone, or imidazole, Y and Y' are linker groups, R and R' are hydrophobic groups as defined herein independently having 2-20 carbon atoms, or alkoxyl ethyl groups, —(CH$_2$)$_l$—O—CH$_2$—CH$_3$, wherein l is 2, 3, or 4 (a preferred alkoxy ethyl group is a 2-ethoxyethyl group, —(CH$_2$)$_2$—O—CH$_2$—CH$_3$, R1, R2, R3, and R4 are independently selected from hydrogen (—H) and methyl (—CH$_3$), m and p are integers greater than zero (0), n and q are integers greater than or equal to zero (0), and the ratio (m+n)/(p+q) is 1-9 (50-90% amines) and more preferably 1.5-4 (60-80% amines).

A preferred R group is a hydrophobic group having 2-6 carbon atoms.

Linker groups Y and Y' are uncharged and link the nitrogen to the vinyl ester via 1-24 carbon atoms, one or more of which may be substituted for heteroatoms. In a preferred embodiment, Y and Y' independently contain 1-12 carbon atoms, one or more of which may be substituted for heteroatoms. In one embodiment, Y and Y' are independently selected from —(CH$_2$)$_x$— and —(CH$_2$—CH$_2$—O)$_z$—(CH$_2$)$_x$—, wherein x and z are independently 1, 2, 3, 4, 5, or 6.

In one embodiment, the present invention is directed to vinyl ester random copolymers of formula (Ia):

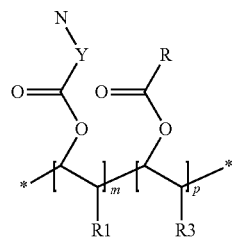

wherein:

N is a primary amine having the form —NH$_2$,

Y is a linker group as described above,

R is a hydrophobic group as defined herein having 2-6 carbon atoms or an alkoxyl ethyl group, —(CH$_2$)$_l$—O—CH$_2$—CH$_3$, wherein l is 2, 3, or 4 (preferably 2-ethoxyethyl), R1 and R3 are independently selected from hydrogen (—H) and methyl (—CH$_3$), m is an integer greater than zero (0), p is an integer greater than zero (0), the ratio m/p is 1-9 (50-90% amines) and more preferably 1.5-4 (60-80% amines).

The polymers according to the present invention can be generally obtained as described herein and using methods known to the person of ordinary skill in the art of organic or medicinal chemistry. The polymers are polymerized from hydrophobic group-containing vinyl ester monomers and protected amine-containing vinyl ester monomers. Polymerization to form the polymers of the invention is preferably carried out using Reversible Addition-Fragmentation chain Transfer (RAFT) polymerization. In one embodiment, the RAFT polymerization is carried out using Malonate N,N-diphenyl dithiocarbamate (MDP-DTC). Polymer synthesis is performed using protected amine monomers. Deprotection of the amine yields the amine-containing polymers of formulae (I) or (Ia), wherein N is —NH$_2$. As an example, compounds of formula (Ia), wherein Y is —(CH$_2$)$_3$—, R1 is hydrogen, R3 is hydrogen, and R is —(CH$_2$)$_3$—CH$_3$ and can be obtained using compounds 3 and 8 as starting material.

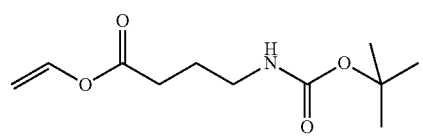

3

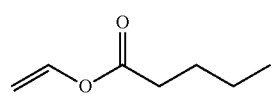

8

Synthesis of vinyl ester monomers 3 and 8 are described below.

Reversible Addition-Fragmentation chain Transfer (RAFT) polymerization is a form of controlled radical polymerization. More specifically, RAFT is a type of living polymerization involving a conventional radical polymerization in the presence of a reversible chain transfer reagent. RAFT polymerization permits synthesis of a wide range of polymers with controlled molecular weight and low polydispersity (PDI), between 1.05 and 1.6, for many monomers. Poly(vinyl ester)s of the invention preferably have a polydispersity less than 1.5 and more preferably less than 1.4 or 1.3. Fractionation may be used to further reduce polydispersity. RAFT polymerization is described in WO9504026, WO9801478, WO9905099, WO9931144, WO10083569, U.S. Pat. No. 6,291,620, U.S. Pat. No. 6,376,626, U.S. Pat. No. 6,642,318, and U.S. Pat. No. 6,747,111. Polymers with molecular weights greater than 20,000 and low polydisperity are also possible with RAFT polymerization and are preferred for in vivo delivery. In order for macromolecules to circulate through the blood stream effectively and to not be cleared by the kidneys, molecular weights above 30,000-50,000 are often preferred.

It is an essential feature of the unmodified amphipathic poly(vinyl ester) random copolymers of the invention that they are membrane active; i.e., they are capable of disrupting plasma membranes or lysosomal/endocytic membranes. Membrane activity, however, can lead to toxicity when the polymer is administered in vivo. Polyamines also interact readily with many anionic components in vivo, leading to undesired bio-distribution. Therefore, reversible inhibition of membrane activity of the polyamine is used for in vivo use. This inhibition is accomplished through reversible physiologically labile attachment of masking agents to polymer amines to form a reversibly masked membrane active poly(vinyl ester), i.e. herein also termed a delivery polymer. In addition to inhibiting membrane activity, the masking agents shield the polymer from non-specific interactions, reduce serum interactions, increase circulation time, or provide cell-specific interactions, i.e. targeting. The process of reversible modification also reduces positive charge to form a near neutral charge polymer. As used herein, labile means that linkage of the masking agent to the polymer is readily cleaved under conditions typically present under physiological conditions. As used herein, reversible means that cleavage of the bond linking the masking agent to the polymer results in restoration of the polymer amine to the pre-modified state, i.e. to a primary amine.

A preferred reversible physiologically labile linkage comprises: a physiologically labile covalent bond or a covalent bond cleavable under mammalian intracellular conditions. A preferred labile covalent bond comprises a pH labile bond. A preferred pH labile physiologically labile linkage comprises a maleamate. Another preferred physiologically labile linkage comprises an enzymatically cleavable linkage. A preferred enzymatically cleavable linkage is a peptide (amide) bond. A preferred peptide linkage comprises a dipeptide-amidobenzyl-carbonate as described in U.S. patent application Ser. No. 13/326,433, incorporated herein by reference.

It is an essential feature of the masking agents that, in aggregate, they inhibit membrane activity of the polymer, shield the polymer from non-specific interactions (reduce serum interactions, increase circulation time), and provide in vivo cell targeting. The membrane active poly(vinyl ester)s of the invention are membrane active in the unmodified (unmasked) state and not membrane active (inactivated) in the modified (masked) state. A sufficient number of masking agents are linked to the polymer to achieve the desired level of inactivation. The desired level of modification of a poly(vinyl ester) by attachment of masking agent(s) is readily determined using appropriate membrane activity assays. For example, if the poly(vinyl ester) possesses membrane activity in a given assay, a sufficient level of masking agent is linked to the polymer to achieve the desired level of inhibition of membrane activity in that assay. Masking requires modification of ≥50%, ≥60%, ≥70%, or ≥80% of the amine groups on the polymer, as determined by the quantity of amines on the polymer in the absence of any masking agents. It is also a preferred characteristic of masking agents that their attachment to the polymer reduces net charge of the polymer, thus forming a more neutral delivery polymer. It is desirable that the masked polymer retain aqueous solubility.

As used herein, a membrane active poly(vinyl ester) of the invention is masked if the modified polymer does not exhibit membrane activity and exhibits cell-specific (e.g., hepatocyte) targeting in vivo. A membrane active poly(vinyl ester) of the invention is reversibly masked if cleavage of linkages attaching the masking agents to the polymer results in restoration of amines on the poly(vinyl ester) thereby restoring membrane activity.

It is another essential feature that the masking agents are linked to the membrane active poly(vinyl ester) through reversible physiologically labile covalent bonds. By using reversible physiologically labile linkages or bonds, the masking agents can be cleaved from the polymer in vivo, thereby unmasking the polymer and restoring activity of the unmasked polymer. By choosing an appropriate reversible linkage, it is possible to form a conjugate that restores activity of the membrane active polymer after it has been delivered or targeted to a desired cell type or cellular location. Reversibility of the linkages provides for selective activation of the membrane active polymer. Suitable reversible covalent linkages contain reversible labile bonds which may be selected from the group comprising: physiologically labile bonds, cellular physiologically labile bonds, protease sensitive linkages, pH labile bonds, very pH labile bonds, and extremely pH labile bonds.

As used herein, a masking agent comprises a compound having an cell targeting group or a steric stabilizer and an amine-reactive group wherein reaction of the amine-reactive group with an amine on a poly(vinyl ester) results in linkage of the targeting group or steric stabilizer to the polymer via a reversible physiologically labile covalent bond. Preferably, the masking agent is charge neutral. A preferred targeting group is an Asialoglycoprotein Receptor (ASGPr) targeting group. An ASGPr targeting group is a group, typically a saccharide, having affinity for the asialoglycoprotein receptor. A preferred steric stabilizer is a polyethylene glycol (PEG). Preferred masking agents of the invention are able to modify the poly(vinyl ester)s of the invention (form a reversible bond with the polymer) in aqueous solution.

A preferred amine-reactive group comprises a disubstituted maleic anhydride. A preferred masking agent is represented by the structure:

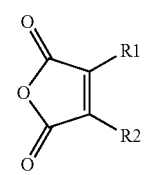

wherein $R^1$ is an alkyl group such as a methyl group (—$CH_3$), ethyl group (—$CH_2CH_3$), or propyl group (—$CH_2CH_2CH_3$), and $R^2$ comprises a neutral targeting group or a neutral steric stabilizer. More preferably, the targeting agent and steric stabilizer are uncharged. Monosubstituted maleic anhydrides, in which R1 or R2 is a hydrogen, yield linkages which are not suitable for the described invention. While reaction of a maleic anhydride with an amine yields a β carboxyl group, this β carboxyl does not exhibit a full apparent negative charge (Rozema et al. Bioconjugate Chem. 2003, 14, 51-57). Therefore, maleic anhydride-based masking agents in which R1 and R2 are charge neutral can be used to neutralize a polyamine without imparting high negative charge.

In one embodiment, poly(vinyl ester) polyamines of the invention are reversibly modified by reaction with a plurality of disubstituted maleic anhydrides. The present invention therefore provides random copolymers of formulae:

chains. In a preferred dipeptide, R1 is a hydrophobic amino acid side chain and R2 is an uncharged hydrophilic amino acid side chain. A preferred hydrophobic amino acid is phenylalanine, valine, isoleucine, leucine, alanine, or tryptophan. A preferred uncharged hydrophilic amino acid is asparagine, glutamine, or citrulline. A more preferred hydrophobic amino acid is phenylalanine or valine. A more preferred uncharged hydrophilic amino acid is citrulline. A

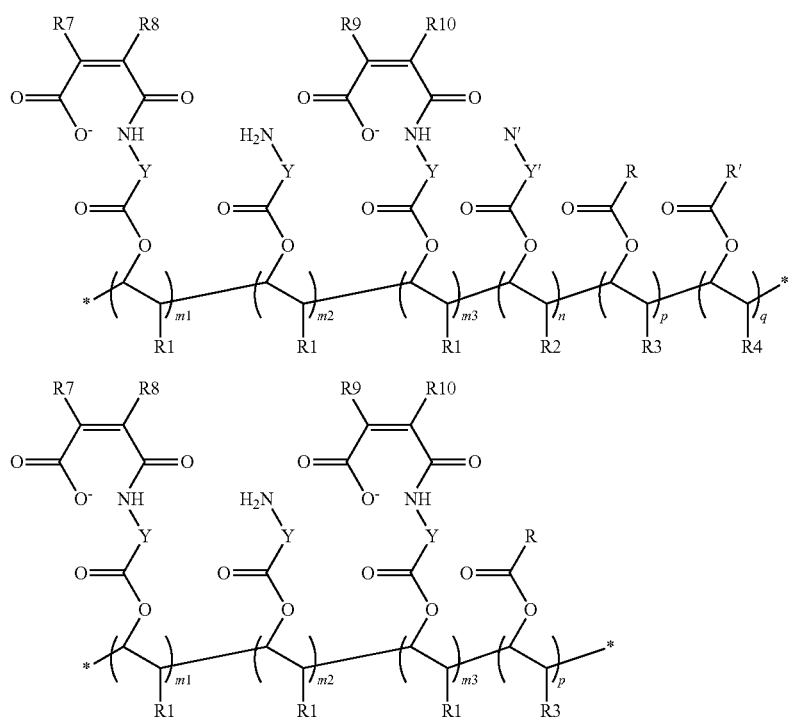

formula (II)

formula (IIa)

wherein N', Y, Y', R, R', R1, R2, R3, R4, m, n, p, q have the meanings given for formulae (I) and (Ia) above,
  m1 is an integer≥zero and ≤m of formula (I) or (Ia),
  m3 is an integer≥zero and ≤m of formula (I) or (Ia),
  m1+m2+m3=m of formulae (I) or (Ia),
  m1+m3 is an integer≥m2 [i.e., ≥0.5×m of formulae (I) or (Ia) and ≤m of formula (I) or (Ia)],
  R7 is an alkyl group and R8 comprises a neutral targeting group or R8 is an alkyl group and R7 comprises a neutral targeting group, and
  R9 is an alkyl group and R10 comprises a neutral steric stabilizer or R10 is an alkyl group and R9 comprises a neutral steric stabilizer.

Another preferred masking agent comprises a protease sensitive dipeptide-amidobenzyl-carbonate represented by the structure:

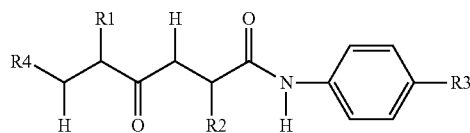

wherein R4 comprises a neutral, preferably uncharged, targeting ligand or steric stabilizer, R3 comprises an amine reactive carbonate group, and R1 and R2 are amino acid side preferred activated carbonate is a para-nitrophenol. However, other amine reactive carbonates known in the art are readily substituted for the para-nitrophenol. Reaction of the activated carbonate with an amine connects the targeting ligand or steric stabilizer to the membrane active polyamine via a peptidase cleavable dipeptide-amidobenzyl carbamate linkage. Enzyme cleavage of the dipeptide, between the amino acid and the amidobenzyl group removes R4 from the polymer and triggers an elimination reaction which results in regeneration of the polymer amine.

Reaction of a dipeptide-amidobenzyl-carbonate masking agent with an amine of the poly(vinyl ester) results in reversible modification of the poly(vinyl ester). Hence, provided herein are conjugates comprising the amphipathic membrane active poly(vinyl ester)s described herein masked by modification with dipeptide-amidobenzyl-carbonate masking agents. The polymers so masked have the formula:

formula (III)

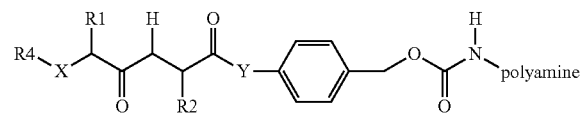

wherein:
X is —NH—, —O—, or —CH$_2$—
Y is —NH— or —O—
R1 is preferably
—(CH$_2$)$_k$-phenyl (k is 1, 2, 3, 4, 5, 6; k=1 phenylalanine),
—CH—(CH$_3$)$_2$ (valine),
—CH$_2$—CH—(CH$_3$)$_2$ (leucine),
—CH(CH$_3$)—CH$_2$—CH$_3$ (isoleucine),
—CH$_3$ (alanine),
—(CH$_2$)$_2$—COOH (glutamic acid),
or

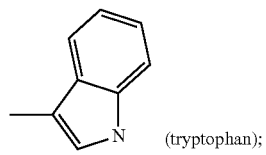 (tryptophan);

R2 is preferably
hydrogen (glycine)
—(CH$_2$)$_3$—NH—C(O)—NH$_2$ (citrulline),
—(CH$_2$)$_4$—N—(CH$_3$)$_2$ (lysine(CH$_3$)$_2$),
—(CH2)$_k$—C(O)—NH$_2$; (k is 1, 2, 3, 4, 5, 6),
—CH$_2$—C(O)—NH$_2$ (asparagine),
—(CH$_2$)$_2$—C(O)—NH$_2$ (glutamine),
—CH$_2$—C(O)—NR$^1$R$^2$ (aspartic acid amide),
—(CH$_2$)$_2$—C(O)—NR$^1$R$^2$ (glutamic acid amide),
—CH$_2$—C(O)—OR$^1$ (aspartic acid ester), or
—(CH$_2$)$_2$—C(O)—OR$^1$ (glutamic acid ester),
R$^1$ and R$^2$ are alkyl groups
R4 comprises a neutral polyethylene glycol or targeting ligand; and
the polyamine is an amphipathic membrane active poly(vinyl ester).

While the structure above indicates a single dipeptide masking agent linked to the polymer, in practice of the invention, 50% to 90% or more of polymer amines are modified by dipeptide masking agents.

The membrane active poly(vinyl ester)s of the invention can be conjugated to masking agents in the presence of an excess of masking agents. The excess masking agent may be removed from the conjugated delivery polymer prior to administration of the delivery polymer.

In one embodiment, the membrane active poly(vinyl ester) polyamine is reversibly masked by attachment of targeting group masking agents or steric stabilizer masking agents to ≥50%, ≥60%, ≥70%, or ≥80% of amines on the polyamine. In another embodiment, the membrane active polyamine is reversibly masked by attachment of a combination of targeting group masking agents and steric stabilizer masking agents to ≥50%, ≥60%, ≥70%, or ≥80% of amines on the polyamine. In another embodiment, the targeting group masking agents comprise a targeting group linked to an amine-reactive group via a PEG linker. For membrane active polyamine masking with both targeting group masking agents and steric stabilizer masking agents, a ratio of steric stabilizer to targeting group is about 0-4:1, more preferably about 0.5-2:1. In another embodiment, there are about 1.3-2 steric stabilizer masking agents to about 1 targeting group agent.

In a further embodiment of the present invention, there is provided a conjugate of the polymers of formula (I) or (Ia) covalently attached to a biologically active compound, preferably an RNA interference polynucleotide. Preferably, the polymer is covalently linked to the polynucleotide by a physiologically labile linkage. A preferred physiologically labile linkage is orthogonal to the masking agent physiologically labile linkage. A suitable physiologically labile linkage may be selected from the group comprising: physiologically labile bonds, cellular physiologically labile bonds, pH labile bonds, very pH labile bonds, extremely pH labile bonds, enzymatically cleavable bonds (including appropriate ester, amide, and phopshodiester bonds), and disulfide bonds.

We have found that by attaching the polynucleotide to the polymer via a reversible linker that is broken after the polynucleotide is delivered to the cell, it is possible to deliver a functionally active polynucleotide to a cell in vivo. The labile linker is selected such that it undergoes a chemical transformation (e.g., cleavage) when present in certain physiological conditions, (e.g., the reducing environment of the cell cytoplasm). Attachment of a polynucleotide to poly(vinyl ester) of the invention enhances delivery of the polynucleotide to a cell in vivo. Release of the polynucleotide from the polymer, by cleavage of the labile linkage, facilitates interaction of the polynucleotide with the appropriate cellular components for activity.

The RNAi polynucleotide-polymer conjugate is formed by linking the RNAi polynucleotide to the polymer via a physiologically labile covalent bond. The polynucleotide is synthesized or modified such that it contains a reactive group A. The polymer is also synthesized or modified such that it contains a reactive group B. Reactive groups A and B are chosen such that they can be linked via a physiologically labile covalent linkage using methods known in the art. The polymer may be linked to the 3' or the 5' end of the RNAi polynucleotide. For siRNA polynucleotides, the targeting group may be linked to either the sense strand or the antisense strand, though the sense strand is preferred.

Conjugation of the RNAi polynucleotide to a side chain primary amine of polymers (I) or (Ia) results in polymers of formula (IV) or (IVa).

formula (IV)

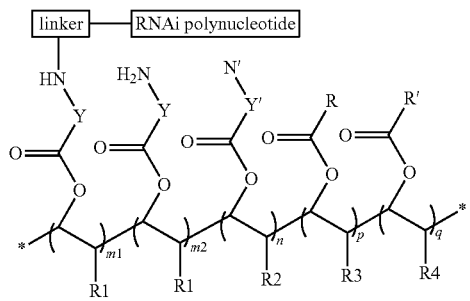

formula (IVa)

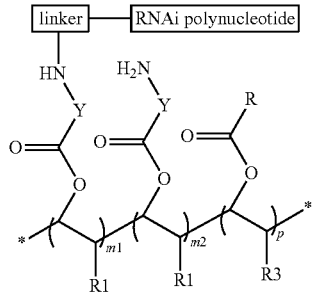

wherein N', Y, Y', R, R', R1, R2, R3, R4, m, n, p, q have the meanings given for formulae (I) and (Ia) above, m1 is 1, 2, 3, or 4,
m1+m2=m of formula (I) or (Ia); and
the linker comprises a physiologically labile linker.

In another embodiment, the RNAi polynucleotide is conjugated to a polymer backbone terminus as illustrated in formulae (V) and (Va). The polynucleotide may also be attached to the other terminus.

formula (V)

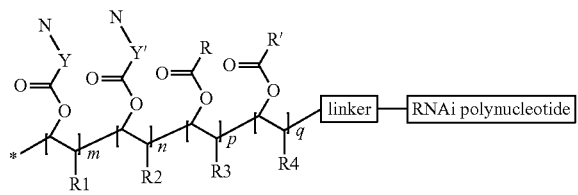

formula (Va)

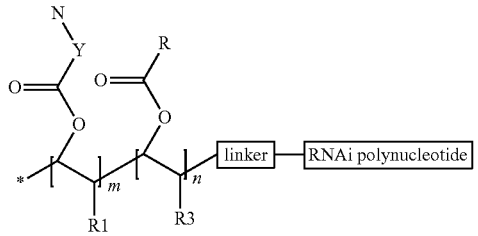

wherein N, N', Y, Y', R, R', R1, R2, R3, R4, m, n, p, q have the meanings given for formulae (I) and (Ia) above, and the linker comprises a physiologically labile linker.

In a further embodiment of the present invention, there are provided conjugates of the polymers of formulae (II), (IIa), and (III) covalently attached to a biologically active compound, preferably an RNA interference polynucleotide, as shown above for the unmodified polymers. Preferably, the polymer is covalently linked to the polynucleotide by a physiologically labile linkage.

The polynucleotide can be attached to the polymer in the presence of an excess of polymer. The excess polymer may aid in formulation of the polynucleotide-polymer conjugate. The excess polymer may reduce aggregation of the conjugate during formulation of the conjugate. The polynucleotide-polymer conjugate may be separated from the excess polymer prior to administration of the conjugate to the cell or organism. Alternatively, the polynucleotide-polymer conjugate may be co-administered with the excess polymer to the cell or organism. The excess polymer may be the same as the polymer or it may be different, a helper or boost polymer.

In another embodiment, the invention features compositions for delivering RNA interference polynucleotides to a liver cells in vivo comprising: a polymer of formula (II), (IIa), or (III), and an RNA interference polynucleotide conjugated to a polynucleotide targeting group. The polynucleotide targeting group can be either a hydrophobic group containing at least 20 carbon atoms or a trivalent ASPGr targeting group as described in U.S. Patent Publication 20110207799. The reversibly modified poly(vinyl ester) and the siRNA-conjugate are synthesized separately and may be supplied in separate containers or a single container. The RNA interference polynucleotide is not conjugated to the polymer.

We have found that conjugation of an RNAi polynucleotide to a polynucleotide targeting group, either a hydrophobic group or to a galactose cluster, and co-administration of the RNAi polynucleotide conjugate with the modified poly(vinyl ester) polymers described above provides for efficient, functional delivery of the RNAi polynucleotide to liver cells, particularly hepatocytes, in vivo. By functional delivery, it is meant that the RNAi polynucleotide is delivered to the cell and has the expected biological activity, sequence-specific inhibition of gene expression. Many molecules, including polynucleotides, administered to the vasculature of a mammal are normally cleared from the body by the liver. Clearance of a polynucleotide by the liver wherein the polynucleotide is degraded or otherwise processed for removal from the body and wherein the polynucleotide does not cause sequence-specific inhibition of gene expression is not considered functional delivery.

The RNAi polynucleotide-polynucleotide targeting group conjugate is co-administered with a reversibly modified poly(vinyl ester) of the invention. By co-administered it is meant that the RNAi polynucleotide and the delivery polymer are administered to the mammal such that both are present in the mammal at the same time. The RNAi polynucleotide-targeting group conjugate and the delivery polymer may be administered simultaneously or they may be delivered sequentially. For simultaneous administration, they may be mixed prior to administration. For sequential administration, either the RNAi polynucleotide-targeting group conjugate or the delivery polymer may be administered first.

For RNAi polynucleotide-hydrophobic targeting group conjugates, the RNAi conjugate may be administered up to 30 minutes prior to administration of the delivery polymer. Also for RNAi polynucleotide-hydrophobic targeting group conjugates, the delivery polymer may be administered up to two hours prior to administration of the RNAi conjugate.

For RNAi polynucleotide-galactose cluster targeting group conjugates, the RNAi conjugate may be administered up to 15 minutes prior to administration of the delivery polymer. Also for RNAi polynucleotide-galactose cluster targeting group conjugates, the delivery polymer may be administered up to 15 minutes prior to administration of the RNAi conjugate.

Amphipathic

The poly(vinyl ester) random copolymers of the invention are amphipathic. Amphipathic, or amphiphilic, polymers and have both hydrophilic (polar, water-soluble) and hydrophobic (non-polar, lipophilic, water-insoluble) groups or parts.

As used herein, with respect to amphipathic polymers, a part is defined as a molecule derived when one covalent bond is broken and replaced by hydrogen. For example, in butyl amine, a breakage between the carbon and nitrogen bonds, and replacement with hydrogens, results in ammonia (hydrophilic) and butane (hydrophobic). If 1,4-diaminobutane is cleaved at nitrogen-carbon bonds, and replaced with hydrogens, the resulting molecules are again ammonia (2×) and butane. However, 1,4,-diaminobutane is not considered amphipathic because formation of the hydrophobic part requires breakage of two bonds.

Membrane Active

As used herein, membrane active polymers are surface active, amphipathic polymers that are able to induce one or more of the following effects upon a biological membrane: an alteration or disruption of the membrane that allows non-membrane permeable molecules to enter a cell or cross the membrane, pore formation in the membrane, fission of membranes, or disruption or dissolving of the membrane. As used herein, a membrane, or cell membrane, comprises a lipid bilayer. The alteration or disruption of the membrane can be functionally defined by the polymer's activity in at least one the following assays: red blood cell lysis (hemolysis), liposome leakage, liposome fusion, cell fusion, cell lysis, and endosomal release. Membrane active polymers that can cause lysis of cell membranes are also termed membrane lytic polymers. Polymers that preferentially cause disruption of endosomes or lysosomes over plasma membrane are considered endosomolytic. The effect of membrane active polymers on a cell membrane may be transient. Membrane active polymers possess affinity for the membrane and cause a denaturation or deformation of bilayer structures. Membrane active polymers may be synthetic or non-natural amphipathic polymers.

Delivery of a polynucleotide to a cell is mediated by the membrane active polymer disrupting or destabilizing the plasma membrane or an internal vesicle membrane (such as an endosome or lysosome), including forming a pore in the membrane, or disrupting endosomal or lysosomal vesicles thereby permitting release of the contents of the vesicle into the cell cytoplasm.

Endosomolytic

Endosomolytic polymers are polymers that, in response to a change in pH, are able to cause disruption or lysis of an endosome or provide for release of a normally cell membrane impermeable compound, such as a polynucleotide or protein, from a cellular internal membrane-enclosed vesicle, such as an endosome or lysosome. Endosomolytic polymers undergo a shift in their physico-chemical properties over a physiologically relevant pH range (usually pH 5.5-8). This shift can be a change in the polymer's solubility or ability to interact with other compounds or membranes as a result in a shift in charge, hydrophobicity, or hydrophilicity. Exemplary endosomolytic polymers have pH-labile groups or bonds. A reversibly masked membrane active poly(vinyl ester), wherein the masking agents are attached to the polymer via pH labile bonds, can therefore be considered to be an endosomolytic polymer.

Hydrophilic Group

Hydrophilic group indicates in qualitative terms that the chemical group is water-preferring. Typically, such chemical groups are water soluble, and are hydrogen bond donors or acceptors with water. A hydrophilic group can be charged or uncharged. Charged groups can be positively charged (anionic) or negatively charged (cationic) or both (zwitterionic). Examples of hydrophilic groups include the following chemical moieties: carbohydrates, polyoxyethylene, certain peptides, oligonucleotides, amines, amides, alkoxy amides, carboxylic acids, sulfurs, and hydroxyls.

Hydrophobic Group

Hydrophobic group indicates in qualitative terms that the chemical group is water-avoiding. Typically, such chemical groups are not water soluble, and tend not to form hydrogen bonds. Hydrophobic groups dissolve in fats, oils, lipids, and non-polar solvents and have little to no capacity to form hydrogen bonds. Hydrocarbons containing two (2) or more carbon atoms, certain substituted hydrocarbons, cholesterol, and cholesterol derivatives are examples of hydrophobic groups and compounds.

Hydrophobic groups are preferably hydrocarbons, containing only carbon and hydrogen atoms. However, non-polar substitutions or non-polar heteroatoms which maintain hydrophobicity, and include, for example fluorine, may be permitted. The term includes aliphatic groups, aromatic groups, acyl groups, alkyl groups, alkenyl groups, alkynyl groups, aryl groups, aralkyl groups, aralkenyl groups, and aralkynyl groups, each of which may be linear, branched, or cyclic. The term hydrophobic group also includes: sterols, steroids, cholesterol, and steroid and cholesterol derivatives. As used herein, lower hydrophobic monomers or groups comprise hydrophobic groups having two (2) to six (6) carbon atoms. As used herein, medium hydrophobic monomers or groups comprise hydrophobic groups having seven (7) to eleven (11) carbon atoms. As used herein, higher hydrophobic monomers or groups comprise hydrophobic groups having twelve (12) to thirty-six (36) or more carbon atoms.

Targeting Group

Targeting groups or moieties enhance the pharmacokinetic or biodistribution properties of a conjugate to which they are attached to improve cell-specific distribution and cell-specific uptake of the conjugate. Targeting groups enhance the association of molecules with a target cell. Thus, targeting groups can enhance the pharmacokinetic or biodistribution properties of a conjugate to which they are attached to improve cellular distribution and cellular uptake of the conjugate. Binding of a targeting group, such as a ligand, to a cell or cell receptor may initiate endocytosis. Targeting groups may be monovalent, divalent, trivalent, tetravalent, or have higher valency. Targeting groups may be selected from the group comprising: compounds with affinity to cell surface molecule, cell receptor ligands, and antibodies, antibody fragments, and antibody mimics with affinity to cell surface molecules. A preferred targeting group comprises a cell receptor ligand. A variety of ligands have been used to target drugs and genes to cells and to specific cellular receptors. Cell receptor ligands may be selected from the group comprising: carbohydrates, glycans, saccharides (including, but not limited to: galactose, galactose derivatives, mannose, and mannose derivatives), vitamins, folate, biotin, aptamers, and peptides (including, but not limited to: RGD-containing peptides, insulin, EGF, and transferrin).

ASGPr Targeting Group

Galactose and galactose derivates have been used to target molecules to hepatocytes in vivo through their binding to the asialoglycoprotein receptor (ASGPr) expressed on the surface of hepatocytes. As used herein, an ASGPr targeting group comprises a galactose and galactose derivative (structural analog) having affinity for the ASGPr equal to or greater than that of galactose. Binding of galactose targeting moieties to the ASGPr(s) facilitates cell-specific targeting of the delivery polymer to hepatocytes and endocytosis of the delivery polymer into hepatocytes.

ASGPr targeting moieties may be selected from the group comprising: lactose, galactose, N-acetylgalactosamine (GalNAc), galactosamine, N-formylgalactosamine, N-acetyl-galactosamine, N-propionylgalactosamine, N-n-butanoylgalactosamine, N-iso-butanoyl-galactosamine, oligosaccharides, saccharide clusters (such as: Tyr-Glu-Glu-(aminohexyl GalNAc)$_3$, lysine-based galactose clusters, and cholane-based galactose clusters) (Iobst, S. T. and Drickamer, K. *J.B.C.* 1996, 271, 6686). ASGPr targeting moieties can be monomeric (e.g., having a single galactosamine) or multimeric (e.g., having multiple galactosamines). Further suitable conjugates can include oligosaccharides that can bind to carbohydrate recognition domains (CRD) found on the asialoglycoprotein-receptor (ASGP-R). Example conjugate moieties containing oligosaccharides and/or carbohydrate complexes are provided in U.S. Pat. No. 6,525,031.

In some embodiments, an ASGPr targeting group is linked to an amine-reactive group, such as a maleic anhydride, through a PEG linker as illustrated by the structure:

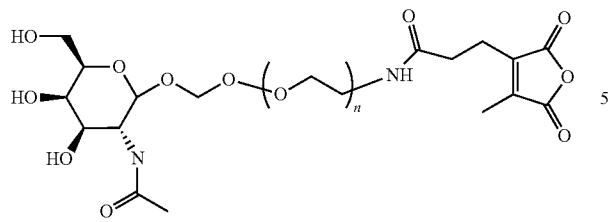 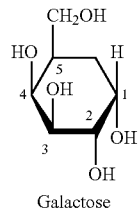

Galactose wherein n is an integer between 1 and 19 (inclusive).

In one embodiment, an ASGPr targeting group comprises a galactose cluster (galactose cluster targeting group). As used herein, a galactose cluster comprises a molecule having two to four terminal galactose derivatives. A terminal galactose derivative is attached to a molecule through its C-1 carbon. A preferred galactose cluster has three terminal galactosamines or galactosamine derivatives each having affinity for the asialoglycoprotein receptor. A more preferred galactose cluster has three terminal N-acetyl-galactosamines. Other terms common in the art include tri-antennary galactose, tri-valent galactose and galactose trimer. It is known that tri-antennary galactose derivative clusters are bound to the ASGPr with greater affinity than bi-antennary or mono-antennary galactose derivative structures (Baenziger and Fiete, 1980, Cell, 22, 611-620; Connolly et al., 1982, J. Biol. Chem., 257, 939-945).

A galactose cluster contains three galactose derivatives each linked to a central branch point. The galactose derivatives are attached to the central branch point through the C-1 carbons of the saccharides. The galactose derivative is preferably linked to the branch point via linkers or spacers. A preferred spacer is a flexible hydrophilic spacer (U.S. Pat. No. 5,885,968; Biessen et al. J. Med. Chem. 1995 Vol. 39 p. 1538-1546). A preferred flexible hydrophilic spacer is a PEG spacer. A preferred PEG spacer is a $PEG_3$ spacer. The branch point can be any small molecule which permits attachment of the three galactose derivatives and further permits attachment of the branch point to the RNAi polynucleotide. An exemplary branch point group is a di-lysine. A di-lysine molecule contains three amine groups through which three galactose derivatives may be attached and a carboxyl reactive group through which the di-lysine may be attached to the RNAi polynucleotide.

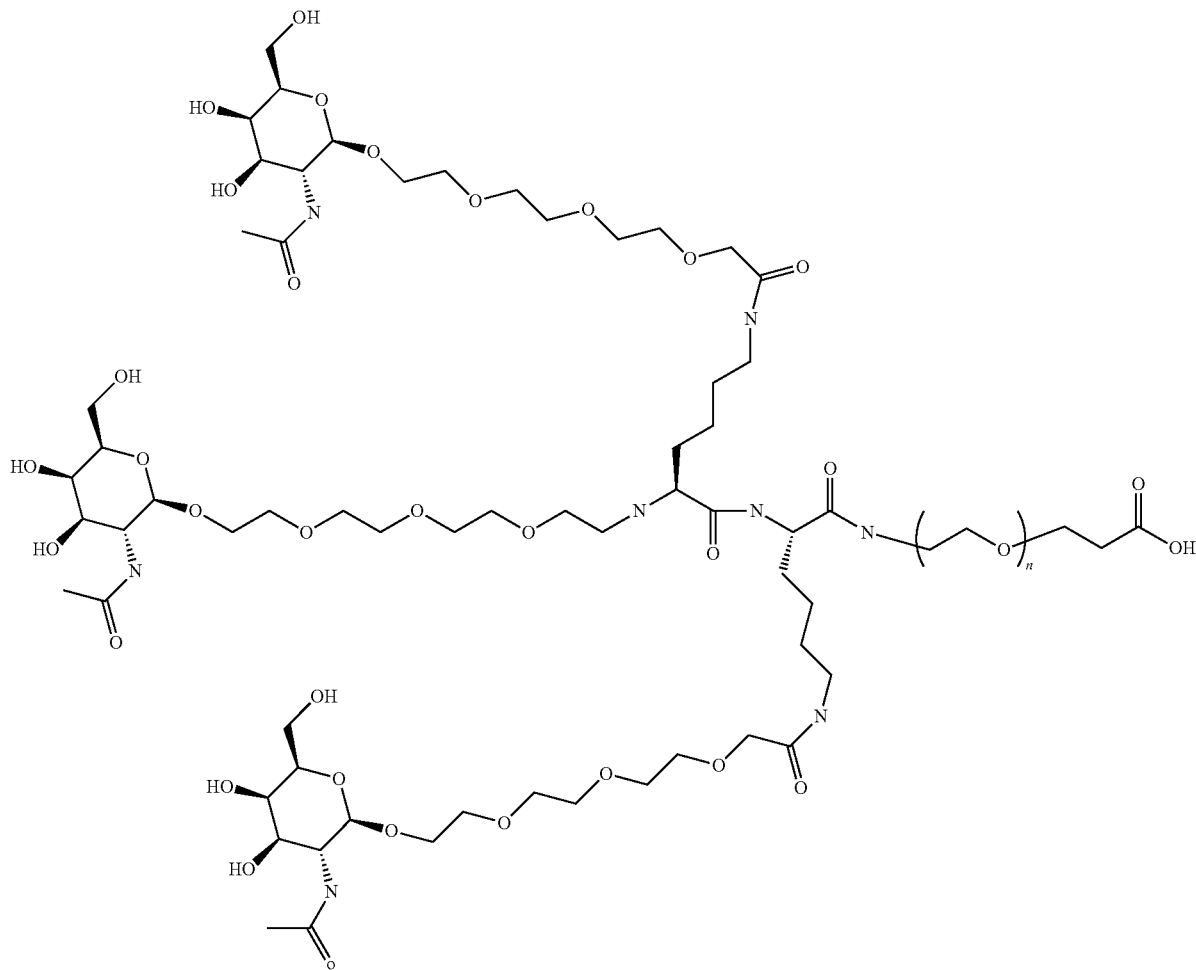

Galactose Cluster with PEG Spacer Between
Branch Point and Nucleic Acid

Steric Stabilizer

As used herein, a steric stabilizer is a non-ionic hydrophilic polymer (either natural, synthetic, or non-natural) that prevents or inhibits intramolecular or intermolecular interactions of a polymer to which it is attached relative to the polymer containing no steric stabilizer. A steric stabilizer hinders a polymer to which it is attached from engaging in electrostatic interactions. Electrostatic interaction is the non-covalent association of two or more substances due to attractive forces between positive and negative charges. Steric stabilizers can inhibit interaction with blood components and therefore opsonization, phagocytosis, and uptake by the reticuloendothelial system. Steric stabilizers can thus increase circulation time of molecules to which they are attached. Steric stabilizers can also inhibit aggregation of a polymer. A preferred steric stabilizer is a polyethylene glycol (PEG) or PEG derivative. As used herein, a preferred PEG can have about 1-500 ethylene glycol monomers, 2-20 ethylene glycol monomers, 5-15 ethylene glycol monomers, or about 10 ethylene glycol monomers. As used herein, a preferred PEG can also have a molecular weight average of about 85-20,000 Daltons (Da), about 200-1000 Da, about 200-750 Da, or about 550 Da. As used herein, steric stabilizers prevent or inhibit intramolecular or intermolecular interactions of a polymer to which it is attached relative to the polymer containing no steric stabilizer in aqueous solution.

A structural analog is a compound having a structure similar to that of another one, but differing from it in respect of a certain component. It can differ in one or more atoms, functional groups, or substructures, which are replaced with other atoms, groups, or substructures. Typically, a structural analog differs in the replacement of a single element, i.e. replacement of one atom or functional group by another atom of a different element or functional group. A structural analog can be imagined to be formed, at least theoretically, from the other compound. As such, a structural analog has a high chemical similarity to the other compound. As typically used in the art, despite structural similarity, structural analogs may have very different physical, chemical, or biochemical properties. However, as used herein with respect to their stated properties, structural analogs have similar physical, chemical, or biochemical properties.

Surface Charge

Zeta potential is a physical property which is exhibited by a particle in suspension and is closely related to surface charge. In aqueous media, the pH of the sample is one of the most important factors that affects zeta potential. When charge is based upon protonation/deprotonation of bases/acids, the charge is dependent on pH. Therefore, a zeta potential value must include the solution conditions, especially pH, to be meaningful. For typical particles, the magnitude of the zeta potential gives an indication of the potential stability of the colloidal system. If all the particles in suspension have a large negative or positive zeta potential, they will tend to repel each other and there will be no tendency for the particles to come together. However, if the particles have low zeta potential values, there will be no force to prevent the particles coming together and flocculating. The general dividing line between stable and unstable suspensions for typical particles is generally taken at either +30 or −30 mV. Particles with zeta potentials more positive than +30 mV or more negative than −30 mV are normally considered stable. Delivery polymers of the described invention exhibit a zeta potential of 20 mV to −20 mV at physiological salt and pH 8, but are colloidally stable in aqueous solution and do not flocculate.

Positive charge, or zeta potential, of a membrane active polyamine is reduced by modification with the masking agents. Polymer charge, especially positive charge, can result in unwanted interactions with serum components or non-target cells. Positive surface charge also plays a role in membrane activity by enhancing interaction of the polymer with negatively charged cell membranes. Therefore, in vivo siRNA delivery vehicles with near neutral net charge or zeta potential are preferred. Delivery polymers of the invention, membrane active polyamines modified by reversible attachment of ASGPr targeting group masking agents and steric stabilizer masking agents, have an apparent surface charge near neutral and are serum stable. More specifically, the delivery polymers of the invention have a zeta potential, measured at pH 8, between +30 and −30 mV, between +20 and −20 mV, between +10 and −10 mV, or between +5 and −5 mV. At pH 7, the net charge of the conjugate is expected to be more positive than at pH 8. Net charge, or surface charge, is a significant factor for in vivo applications.

Labile Linkage

A linkage or linker is a connection between two atoms that links one chemical group or segment of interest to another chemical group or segment of interest via one or more covalent bonds. For example, a linkage can connect a modifying or masking agent to a polymer. Formation of a linkage may connect two separate molecules into a single molecule or it may connect two atoms in the same molecule. The linkage may be charge neutral or may bear a positive or negative charge. A reversible or labile linkage contains a reversible or labile bond. A linkage may optionally include a spacer that increases the distance between the two joined atoms. A spacer may further add flexibility and/or length to the linkage. Spacers may include, but are not be limited to, alkyl groups, alkenyl groups, alkynyl groups, aryl groups, aralkyl groups, aralkenyl groups, aralkynyl groups; each of which can contain one or more heteroatoms, heterocycles, amino acids, nucleotides, and saccharides. Spacer groups are well known in the art and the preceding list is not meant to limit the scope of the invention.

A reversible or labile bond is a covalent bond other than a covalent bond to a hydrogen atom that is capable of being selectively broken or cleaved under conditions that will not break or cleave other covalent bonds in the same molecule. More specifically, a reversible or labile bond is a covalent bond that is less stable (thermodynamically) or more rapidly broken (kinetically) under appropriate conditions than other non-labile covalent bonds in the same molecule. Cleavage of a labile bond within a molecule may result in the formation of two molecules. For those skilled in the art, cleavage or lability of a bond is generally discussed in terms of half-life ($t_{1/2}$) of bond cleavage (the time required for half of the bonds to cleave). Thus, reversible or labile bonds encompass bonds that can be selectively cleaved more rapidly than other bonds in a molecule.

Appropriate conditions are determined by the type of labile bond and are well known in organic chemistry. A labile bond can be sensitive to pH, oxidative or reductive conditions or agents, temperature, salt concentration, the presence of an enzyme (such as esterases, including nucleases, and proteases), or the presence of an added agent. For example, increased or decreased pH is the appropriate conditions for a pH-labile bond.

The rate at which a labile group will undergo transformation can be controlled by altering the chemical constituents of the molecule containing the labile group. For example, addition of particular chemical moieties (e.g., electron acceptors or donors) near the labile group can affect the particular conditions (e.g., pH) under which chemical transformation will occur.

As used herein, a physiologically labile bond is a labile bond that is cleavable under conditions normally encountered or analogous to those encountered within a mammalian body. Physiologically labile linkage groups are selected such that they undergo a chemical transformation (e.g., cleavage) when present in certain physiological conditions.

As used herein, a cellular physiologically labile bond is a labile bond that is cleavable under mammalian intracellular conditions. Mammalian intracellular conditions include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic or hydrolytic enzymes. Physiologically labile bonds that are cleaved under appropriate conditions with a half-life of less than 45 min. are considered very labile. Physiologically labile bonds that are cleaved under appropriate conditions with a half-life of less than 15 min are considered extremely labile.

Chemical transformation (cleavage of the labile bond) occurs when a molecule containing the labile bond reaches an appropriate intra- and/or extra-cellular environment. For example, a pH labile bond may be cleaved when the molecule enters an acidified endosome. Thus, a pH labile bond may be considered to be an endosomal cleavable bond. Enzyme cleavable bonds may be cleaved when exposed to enzymes such as those present in an endosome or lysosome or in the cytoplasm. A disulfide bond may be cleaved when the molecule enters the more reducing environment of the cell cytoplasm. Thus, a disulfide may be considered to be a cytoplasmic cleavable bond.

As used herein, a pH-labile bond is a labile bond that is selectively broken under acidic conditions (pH<7). Such bonds may also be termed endosomally labile bonds, since cell endosomes and lysosomes have a pH less than 7. The term pH-labile includes bonds that are pH-labile, very pH-labile, and extremely pH-labile.

Reaction of an Amine with a Cyclic Anhydride to Form an Amide Acid

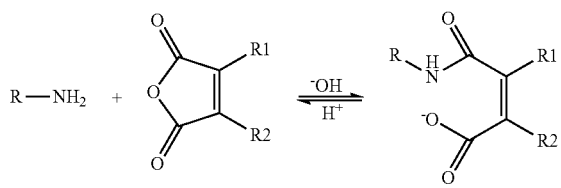

Cleavage of the amide acid to form an amine and an anhydride is pH-dependent and is greatly accelerated at acidic pH. This pH-dependent reactivity can be exploited to form reversible pH-labile bonds and linkers.

Very pH-labile bond: A very pH-labile bond has a half-life for cleavage at pH 5 of less than 45 min. The construction of very pH-labile bonds is well-known in the chemical art.

Extremely pH-labile bonds: An extremely pH-labile bond has a half-life for cleavage at pH 5 of less than 15 min. The construction of extremely pH-labile bonds is well-known in the chemical art.

Disubstituted cyclic anhydrides are particularly useful for modification or attachment of masking agents to membrane active poly(vinyl ester) polymers of the invention. They provide physiologically pH-labile linkages, readily modify amines, and restore those amines upon cleavage in the reduced pH found in cellular endosomes and lysosome. Second, the α or β carboxylic acid group created upon reaction with an amine, appears to contribute only about $\frac{1}{20}^{th}$ of the expected negative charge to the polymer (Rozema et al. Bioconjugate Chemistry 2003). Thus, modification of the polyamine with the disubstituted maleic anhydrides effectively neutralizes the positive charge of the polyamine rather than creates a polymer with high negative charge. Near neutral polymers are preferred for in vivo delivery.

RNAi Polynucleotide-Polynucleotide Targeting Group Conjugate

The RNAi polynucleotide-polynucleotide targeting group conjugate is formed by covalently linking the RNAi polynucleotide to the polynucleotide targeting group. The polynucleotide is synthesized or modified such that it contains a reactive group A. The polynucleotide targeting group is also synthesized or modified such that it contains a reactive group B. Reactive groups A and B are chosen such that they can be linked via a covalent linkage using methods known in the art.

The polynucleotide targeting group may be linked to the 3' or the 5' end of the RNAi polynucleotide. For siRNA polynucleotides, the targeting group may be linked to either the sense strand or the antisense strand, though the sense strand is preferred.

In one embodiment, the polynucleotide targeting group consists of a hydrophobic group. More specifically, the polynucleotide targeting group consists of a hydrophobic group having at least 20 carbon atoms. Hydrophobic groups used as polynucleotide targeting moieties are herein referred to as hydrophobic targeting moieties. Exemplary suitable hydrophobic groups may be selected from the group comprising: cholesterol, dicholesterol, tocopherol, ditocopherol, didecyl, didodecyl, dioctadecyl, didodecyl, dioctadecyl, isoprenoid, and choleamide.

The hydrophobic targeting group may be attached to the 3' or 5' end of the RNAi polynucleotide using methods known in the art. For RNAi polynucleotides having two strands, such as siRNA, the hydrophobic group may be attached to either strand.

The galactose cluster may be attached to the 3' or 5' end of the RNAi polynucleotide using methods known in the art. For RNAi polynucleotides having two strands, such as siRNA, the galactose cluster may be attached to either strand.

Polynucleotide

The term polynucleotide, or nucleic acid or polynucleic acid, is a term of the art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. A non-natural or synthetic polynucleotide is a polynucleotide that is polymerized in vitro or in a cell free system and contains the same or similar bases but may contain a backbone of a type other than the natural ribose or deoxyribose-phosphate backbone. Polynucleotides can be synthesized using any known technique in the art. Polynucleotide backbones known in the art include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups on the nucleotide such as, but not limited to, amines, alcohols, thiols, carboxylates, and alkylhalides. The term base encompasses any of the known base analogs of DNA and RNA. A polynucleotide may contain ribonucleotides, deoxyribonucleotides, synthetic nucleotides, or any suitable combination. Polynucleotides may be polymerized in vitro, they may be recombinant, contain chimeric sequences, or derivatives of these groups. A polynucleotide may include a terminal cap group at the 5'-end, the 3'-end, or both the 5' and 3' ends. The cap group can be, but is not limited to, an inverted deoxy abasic group, an inverted deoxy thymidine group, a thymidine group, or 3' glyceryl modification.

An RNA interference (RNAi) polynucleotide is a molecule capable of inducing RNA interference through interaction with the RNA interference pathway machinery of mammalian cells to degrade or inhibit translation of messenger RNA (mRNA) transcripts of a transgene in a sequence specific manner. Two primary RNAi polynucleotides are small (or short) interfering RNAs (siRNAs) and micro RNAs (miRNAs). RNAi polynucleotides may be selected from the group comprising: siRNA, miRNA, double-strand RNA (dsRNA), short hairpin RNA (shRNA), and expression cassettes encoding RNA capable of inducing RNA interference. siRNA comprises a double stranded structure typically containing 15-50 base pairs and preferably 21-25 base pairs and having a nucleotide sequence identical (perfectly complementary) or nearly identical (partially complementary) to a coding sequence in an expressed target gene or RNA within the cell. An siRNA may have dinucleotide 3' overhangs. An siRNA may be composed of two annealed polynucleotides or a single polynucleotide that forms a hairpin structure. An siRNA molecule of the invention comprises a sense region and an antisense region. In one embodiment, the siRNA of the conjugate is assembled from two oligonucleotide fragments wherein one fragment comprises the nucleotide sequence of the antisense strand of the siRNA molecule and a second fragment comprises nucleotide sequence of the sense region of the siRNA molecule. In another embodiment, the sense strand is connected to the antisense strand via a linker molecule, such as a polynucleotide linker or a non-nucleotide linker. MicroRNAs (miRNAs) are small noncoding RNA gene products about 22 nucleotides long that direct destruction or translational repression of their mRNA targets. If the complementarity between the miRNA and the target mRNA is partial, translation of the target mRNA is repressed. If complementarity is extensive, the target mRNA is cleaved. For miRNAs, the complex binds to target sites usually located in the 3' UTR of mRNAs that typically share only partial homology with the miRNA. A "seed region"—a stretch of about seven (7) consecutive nucleotides on the 5' end of the miRNA that forms perfect base pairing with its target—plays a key role in miRNA specificity. Binding of the RISC/miRNA complex to the mRNA can lead to either the repression of protein translation or cleavage and degradation of the mRNA. Recent data indicate that mRNA cleavage happens preferentially if there is perfect homology along the whole length of the miRNA and its target instead of showing perfect base-pairing only in the seed region (Pillai et al. 2007).

RNAi polynucleotide expression cassettes can be transcribed in the cell to produce small hairpin RNAs that can function as siRNA, separate sense and anti-sense strand linear siRNAs, or miRNA. RNA polymerase III transcribed DNAs contain promoters selected from the list comprising: U6 promoters, H1 promoters, and tRNA promoters. RNA polymerase II promoters include U1, U2, U4, and U5 promoters, snRNA promoters, microRNA promoters, and mRNA promoters.

Lists of known miRNA sequences can be found in databases maintained by research organizations such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al. 2006, Reynolds et al. 2004, Khvorova et al. 2003, Schwarz et al. 2003, Ui-Tei et al. 2004, Heale et al. 2005, Chalk et al. 2004, Amarzguioui et al. 2004).

The polynucleotides of the invention can be chemically modified. Non-limiting examples of such chemical modifications include: phosphorothioate internucleotide linkages, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation. These chemical modifications, when used in various polynucleotide constructs, are shown to preserve polynucleotide activity in cells while at the same time increasing the serum stability of these compounds. Chemically modified siRNA can also minimize the possibility of activating interferon activity in humans.

In one embodiment, a chemically-modified RNAi polynucleotide of the invention comprises a duplex having two strands, one or both of which can be chemically-modified, wherein each strand is about 19 to about 29 nucleotides. In one embodiment, an RNAi polynucleotide of the invention comprises one or more modified nucleotides while maintaining the ability to mediate RNAi inside a cell or reconstituted in vitro system. An RNAi polynucleotide can be modified wherein the chemical modification comprises one or more (e.g., about 1, 2, 3, 4, 5, 6, 7, 8, 9, 10, or more) of the nucleotides. An RNAi polynucleotide of the invention can comprise modified nucleotides as a percentage of the total number of nucleotides present in the RNAi polynucleotide. As such, an RNAi polynucleotide of the invention can generally comprise modified nucleotides from about 5 to about 100% of the nucleotide positions (e.g., 5%, 10%, 15%, 20%, 25%, 30%, 35%, 40%, 45%, 50%, 55%, 60%, 65%, 70%, 75%, 80%, 85%, 90%, 95% or 100% of the nucleotide positions). The actual percentage of modified nucleotides present in a given RNAi polynucleotide depends on the total number of nucleotides present in the RNAi polynucleotide. If the RNAi polynucleotide is single stranded, the percent modification can be based upon the total number of nucleotides present in the single stranded RNAi polynucleotide. Likewise, if the RNAi polynucleotide is double stranded, the percent modification can be based upon the total number of nucleotides present in the sense strand, antisense strand, or both the sense and antisense strands. In addition, the actual percentage of modified nucleotides present in a given RNAi polynucleotide can also depend on the total number of purine and pyrimidine nucleotides present in the RNAi polynucleotide. For example, wherein all pyrimidine nucleotides and/or all purine nucleotides present in the RNAi polynucleotide are modified.

An RNAi polynucleotide modulates expression of RNA encoded by a gene. Because multiple genes can share some degree of sequence homology with each other, an RNAi polynucleotide can be designed to target a class of genes with sufficient sequence homology. Thus, an RNAi polynucleotide can contain a sequence that has complementarity to sequences that are shared amongst different gene targets or are unique for a specific gene target. Therefore, the RNAi polynucleotide can be designed to target conserved regions of an RNA sequence having homology between several genes thereby targeting several genes in a gene family (e.g., different gene isoforms, splice variants, mutant genes, etc.). In another embodiment, the RNAi polynucleotide can be designed to target a sequence that is unique to a specific RNA sequence of a single gene.

The term complementarity refers to the ability of a polynucleotide to form hydrogen bonds with another polynucleotide sequence by either traditional Watson-Crick or other non-traditional types. In reference to the polynucleotide molecules of the present invention, the binding free energy for a polynucleotide molecule with its target (effector binding site) or complementary sequence is sufficient to allow the relevant function of the polynucleotide to proceed, e.g., enzymatic mRNA cleavage or translation inhibition. Determination of binding free energies for nucleic acid molecules is well known in the art (Frier et al. 1986, Turner et al. 1987). A percent complementarity indicates the percentage of bases, in a contiguous strand, in a first polynucleotide molecule which can form hydrogen bonds (e.g., Watson-Crick base pairing) with a second polynucleotide sequence (e.g., 5, 6, 7, 8, 9, 10 out of 10 being 50%, 60%, 70%, 80%, 90%, and 100% complementary). Perfectly complementary means that all the bases in a contiguous strand of a polynucleotide sequence will hydrogen bond with the same number of contiguous bases in a second polynucleotide sequence.

By inhibit, down-regulate, or knockdown gene expression, it is meant that the expression of the gene, as measured by the level of RNA transcribed from the gene or the level of polypeptide, protein, or protein subunit translated from the RNA, is reduced below that observed in the absence of the blocking polynucleotide-conjugates of the invention. Inhibition, down-regulation, or knockdown of gene expression, with a polynucleotide delivered by the compositions of the invention, is preferably below that level observed in the presence of a control inactive nucleic acid, a nucleic acid with scrambled sequence or with inactivating mismatches, or in absence of conjugation of the polynucleotide to the masked polymer.

In Vivo Administration

In pharmacology and toxicology, a route of administration is the path by which a drug, fluid, poison, or other substance is brought into contact with the body. In general, methods of administering drugs and nucleic acids for treatment of a mammal are well known in the art and can be applied to administration of the compositions of the invention. The compounds of the present invention can be administered via any suitable route, most preferably parenterally, in a preparation appropriately tailored to that route. Thus, the compounds of the present invention can be administered by injection, for example, intravenously, intramuscularly, intracutaneously, subcutaneously, or intraperitoneally. Accordingly, the present invention also provides pharmaceutical compositions comprising a pharmaceutically acceptable carrier or excipient.

Parenteral routes of administration include intravascular (intravenous, intraarterial), intramuscular, intraparenchymal, intradermal, subdermal, subcutaneous, intratumor, intraperitoneal, intrathecal, subdural, epidural, and intralymphatic injections that use a syringe and a needle or catheter. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, bile ducts, and ducts of the salivary or other exocrine glands. The intravascular route includes delivery through the blood vessels such as an artery or a vein. The blood circulatory system provides systemic spread of the pharmaceutical.

The described compositions are injected in pharmaceutically acceptable carrier solutions. Pharmaceutically acceptable refers to those properties and/or substances which are acceptable to the mammal from a pharmacological/toxicological point of view. The phrase pharmaceutically acceptable refers to molecular entities, compositions, and properties that are physiologically tolerable and do not typically produce an allergic or other untoward or toxic reaction when administered to a mammal. Preferably, as used herein, the term pharmaceutically acceptable means approved by a regulatory agency of the Federal or a state government or listed in the U.S. Pharmacopeia or other generally recognized pharmacopeia for use in animals and more particularly in humans.

Therapeutic Effect

RNAi polynucleotides may be delivered for research purposes or to produce a change in a cell that is therapeutic. In vivo delivery of RNAi polynucleotides is useful for research reagents and for a variety of therapeutic, diagnostic, target validation, genomic discovery, genetic engineering, and pharmacogenomic applications. We have disclosed RNAi polynucleotide delivery resulting in inhibition of endogenous gene expression in hepatocytes. Levels of a reporter (marker) gene expression measured following delivery of a polynucleotide indicate a reasonable expectation of similar levels of gene expression following delivery of other polynucleotides. Levels of treatment considered beneficial by a person having ordinary skill in the art differ from disease to disease. For example, Hemophilia A and B are caused by deficiencies of the X-linked clotting factors VIII and IX, respectively. Their clinical course is greatly influenced by the percentage of normal serum levels of factor VIII or IX: <2%, severe; 2-5%, moderate; and 5-30% mild. Thus, an increase from 1% to 2% of the normal level of circulating factor in severe patients can be considered beneficial. Levels greater than 6% prevent spontaneous bleeds but not those secondary to surgery or injury. Similarly, inhibition of a gene need not be 100% to provide a therapeutic benefit. A person having ordinary skill in the art of gene therapy would reasonably anticipate beneficial levels of expression of a gene specific for a disease based upon sufficient levels of marker gene results. In the hemophilia example, if marker genes were expressed to yield a protein at a level comparable in volume to 2% of the normal level of factor VIII, it can be reasonably expected that the gene coding for factor VIII would also be expressed at similar levels. Thus, reporter or marker genes serve as useful paradigms for expression of intracellular proteins in general.

The liver is an important target tissue for RNAi therapy given its central role in metabolism (e.g., lipoprotein metabolism in various hypercholesterolemias) and the secretion of circulating proteins (e.g., clotting factors in hemophilia). In addition, acquired disorders such as chronic hepatitis and cirrhosis are common and are also potentially treated by RNAi therapies. A number of diseases or conditions which affect or are affected by the liver are potentially treated through knockdown (inhibition) of gene expression in the liver. Such liver diseases and conditions may be selected from the list comprising: liver cancers (including hepatocellular carcinoma, HCC), viral infections (including hepatitis), metabolic disorders, (including hyperlipidemia and diabetes), fibrosis, and acute liver injury.

The amount (dose) of delivery polymer and RNAi-polynucleotide-conjugate that is to be administered can be determined through routine experimentation. We have shown effective knockdown of gene expression using 0.05-20 mg/kg animal weight of siRNA-conjugate and 1.5-60 mg/kg animal weight delivery polymer. A preferred amount in mice is 0.25-2.5 mg/kg siRNA-conjugate and 1-40 mg/kg delivery polymer. More preferably, about 2-20 mg/kg delivery polymer is administered.

As used herein, in vivo means that which takes place inside an organism and more specifically to a process performed in or on the living tissue of a whole, living multicellular organism (animal), such as a mammal, as opposed to a partial or dead one.

Transfection Reagent

The poly(vinyl ester)s described herein may be used as in vitro transfection reagents. The process of delivering a polynucleotide to a cell in vitro has been commonly termed transfection or the process of transfecting. The term transfecting as used herein refers to the introduction of a polynucleotide from outside a cell to inside the cell such the polynucleotide has biological activity. The polynucleotide may be used for research purposes or to produce a change in a cell that can be therapeutic. The delivery of a polynucleotide can lead to modification of the genetic material present in the target cell.

An in vitro transfection reagent is a compound or composition of compounds that binds to or complexes with oligonucleotides or polynucleotides and mediates their entry into a cell, typically a mammalian cell in vitro. Examples of in vitro transfection reagents include, but are not limited to, protein and polymer complexes (polyplexes), lipids and liposomes (lipoplexes), combinations of polymers and lipids (lipopolyplexes), calcium phosphate precipitates, and dendrimers. Typically, the in vitro transfection reagent has a component with a net positive charge which associates or complexes with, via electrostatic interaction, the negative charge of the oligonucleotide or polynucleotide. Cationic in vitro transfection agents may also condense large nucleic acids. In addition to their utility for in vivo delivery, the poly(acrylate)s described herein can also be used as in vitro transfection reagents. For use as in vitro transfection reagents, the poly(acrylate)s may be masked or unmasked.

EXAMPLES

Example 1

Synthesis of Polymer Monomers

A. Materials

Vinyl acetate (VAc), vinyl butyrate (VBu), Pd (II) acetate, γ-(Boc-amino)butyric acid (Boc-GABA), 5-(Boc-amino) valeric acid (Boc-5-Ava-OH), valeric acid, carbon disulfide, sodium hydride, tetrahydrofuran (THF), dimethylsulfoxide (DMSO), diphenylamine, diethyl chloromalonate, and magnesium sulfate (MgSO$_4$) purchased from Sigma-Aldrich and used without further purification. Monomer 3-tert-butoxycarbonylamino-propionic vinyl ester (BAPVE) was purchased from Sigma-Aldrich prior to dissolving in ethyl acetate and passing through an alumina plug to remove inhibitor.

B. 4-tert-Butoxycarbonylamino-Butyric Acid Vinyl Ester (BABVE) 3 protected amine vinyl ester monomer γ-(Boc-amino)butyric acid 2 (Boc-GABA, 10 g, 49.20 mmol, CAS 57294-38-9) was dissolved in vinyl acetate 1 (450 mL, 4920 mmol, CAS 108-05-4) at room temperature (RT). Once dissolved, Pd (II) acetate (2.21 g, 9.84 mmol, CAS 3375-31-3) and KOH (276 mg, 4.92 mmol, CAS 1310-58-3) were added, and the reaction mixture was stirred overnight at RT. The reaction mixture was then transferred into a large excess of diethyl ether to precipitate black Pd byproduct. The solution plus precipitate was then filtered through celite to remove the black precipitate. The resulting solution was then concentrated to dryness and the product 3 was purified on a silica column using 15% ethyl acetate in hexane eluent. Typical yield was 70-90%. Molecular weight: 229.28.

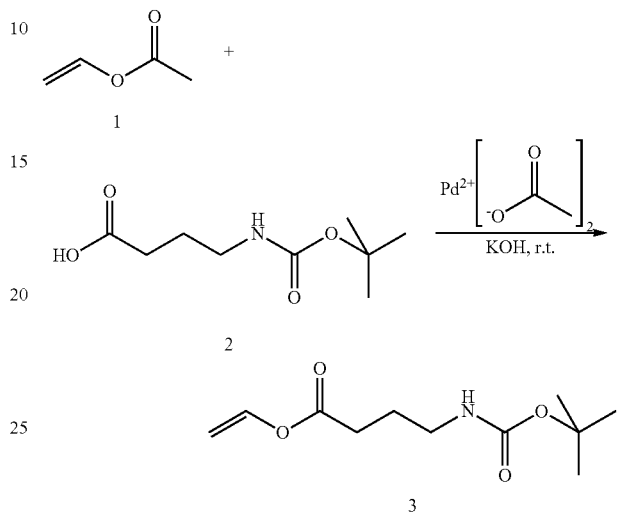

C. 5-tert-Butoxycarbonylamino-Valeric Acid Vinyl Ester (BAVVE) 6 protected amine monomer 5-(Boc-amino)valeric acid 5 (Boc-5-Ava-OH, 10 g, 46.03 mmol, CAS 27219-07-4) was dissolved in vinyl acetate 1 (424 mL, 4603 mmol) at RT. Once dissolved, Pd (II) acetate (2.07 g, 9.21 mmol) and KOH (258 mg, 4.60 mmol) were added and the reaction mixture was stirred overnight at RT. The reaction mixture was then transferred into a large excess of diethyl ether to fully precipitate the black Pd byproduct. The solution plus precipitate was then filtered through celite to remove the black precipitate. The resulting solution was then concentrated to dryness and the product 6 was purified on a silica column using ethyl acetate/hexane eluent. Typical yield was 70-90%. Molecular weight 243.31.

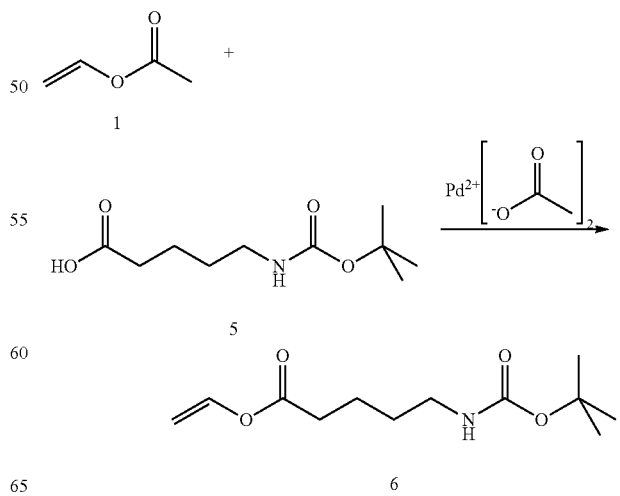

D. Vinyl Valerate (VV) 8 hydrophobic monomer (CAS 5873-43-8)

Valeric acid 7 (5 g, 48.96 mmol, CAS 109-52-4) was dissolved in vinyl acetate 1 (450 mL, 4896 mmol) at RT. Once dissolved, Pd(II) acetate (2.20 g, 9.79 mmol) and KOH (275 mg, 4.89 mmol) were added, and the reaction mixture was stirred overnight at RT. The reaction mixture was then transferred into a large excess of diethyl ether to fully precipitate a black Pd compound. The solution plus precipitate was then filtered through celite to remove the black precipitate. The resulting solution was then concentrated to dryness and the product was purified on a silica column using ethyl acetate/hexane eluent. Typical yield was about 30%. Molecular weight 128.17.

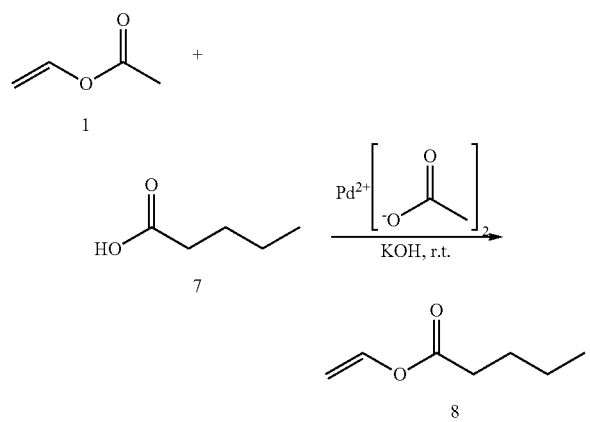

E. Synthesis of 3-(2-tert-butoxycarbonylamino-ethoxy)-propionic vinyl ester (BEPVE)

1) Synthesis of 3-(2-tert-Butoxycarbonylamino-ethoxy)-propionic acid tert-butyl ester In a flame-dried round bottom flask purged with argon, Boc-ethanolamine (10 mL, 64.64 mmol) and tert-butyl acrylate (18.82 mL, 129.28 mmol) were dissolved in dioxane (25 mL) and heated to 25° C. A 60% KOH solution (1.5 mL) was added and the reaction mixture stirred overnight at 25° C. The reaction was monitored by TLC, and more KOH solution was added until most of the starting Boc-ethanolamine was consumed. The reaction mixture was then mixed with DCM, and washed 3 times with deionized water and once with brine. The organic layer was recovered, dried over $Na_2SO_4$, and the solvent removed via rotary evaporation. The resulting oil was purified on a silica column using an ethyl acetate/hexane eluent. Yield=70%.

2) 3-(2-Amino-ethoxy)-propionic acid 3-(2-tert-Butoxycarbonylamino-ethoxy)-propionic acid tert-butyl ester (10 g) was dissolved in a 1:1 trifluoroacetic acid (TFA)/DCM mixture (100 mL) and stirred at room temperature for 1 h. The solvent was then removed on a rotary evaporator and the resulting oil was re-dissolved in DCM and concentrated to dryness. This process was repeated until minimal TFA scent remained before the oil was dried on high vacuum for several hours.

3) 3-(2-tert-Butoxycarbonylamino-ethoxy)-propionic acid 3-(2-Amino-ethoxy)-propionic acid was dissolved in a minimal amount of deionized water before the pH was raised to 8.5 by careful addition of 1 M NaOH. After the pH adjustment, $Boc_2O$ (1 M in THF, 2 eq.) was added dropwise to the solution which was stirred overnight at room temperature. THF was removed by rotary evaporation and reaction mixture dissolved in 1:1 ethyl acetate/methanol and washed with 10% citric acid solution. The aqueous layer was extracted three times with ethyl acetate, and two times with DCM. The organic layers were combined, dried over $Na_2SO_4$, and concentrated to dryness under vacuum. The resulting crude oil was purified by silica gel chromatography with an ethyl acetate/hexane eluent. Yield=30%.

4) 3-(2-tert-Butoxycarbonylamino-ethoxy)-propionic vinyl ester 3-(2-tert-Butoxycarbonylamino-ethoxy)-propionic acid (3.72 g, 15.95 mmol) was dissolved in vinyl acetate (147 mL, 1595 mmol). Pd (II) acetate (716 mg, 3.19 mmol) and KOH (89 mg, 1.59 mmol) were added to the reaction mixture and stirred overnight. The reaction mixture was transferred into a large excess of diethyl ether to fully precipitate the black Pd byproduct. The solution plus precipitate was then filtered through celite to remove the black precipitate. The resulting solution was then concentrated to dryness and the product purified on a silica column using ethyl acetate/hexane eluent. Yield=60%.

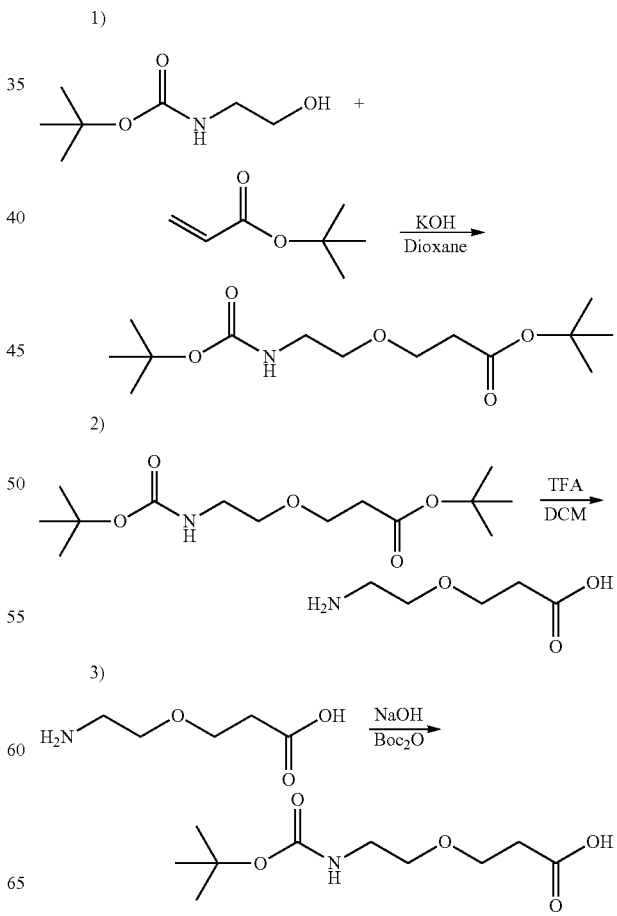

4)

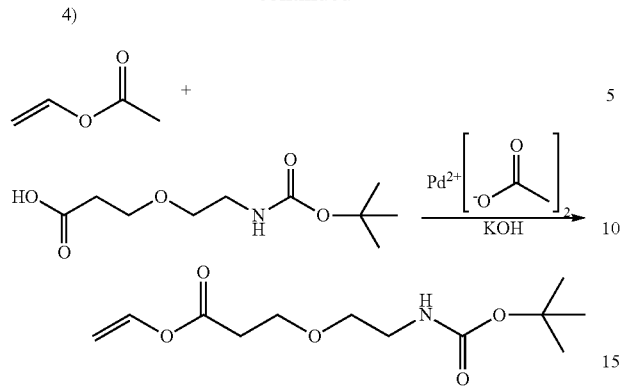

F. Synthesis of malonate N,N-diphenyl dithiocarbamate (MDPD)

MDPD was synthesized according to a procedure described by Shipp et al. Briefly, NaH (1.24 g, 0.0520 mol) was suspended in THF (10 mL) and cooled to 0° C. using an ice bath. A solution of diphenylamine (3.38 g, 0.0200 mol) in DMSO (18 mL) and THF (9 mL) was added and stirred for 1 h at 0° C. Carbon disulfide (2.84 mL, 0.0472 mol) was added and the solution stirred for a further 30 min at 0° C. The solution was then cooled using an ethylene glycol/CO2 bath prior to the addition of diethyl chloromalonate (3.23 mL, 0.0200 mol) and further stirring for 2 h at room temperature. Any remaining NaH was hydrolyzed with methanol and the product was extracted with diethyl ether. Volatiles were then removed and the product was purified using a silica column (ethyl acetate:hexane mix 10:90 to remove diphenylamine impurity, followed by 30:70 to elute product). The product was dried under vacuum to yield a yellow solid (yield 72%).

Example 2

RAFT Copolymerization of Vinyl Ester Monomers to Form Amphiphilic Cationic Poly(Vinyl Ester) Random Copolymers A. Reversible Addition-Fragmentation chain Transfer (RAFT) polymerizations were carried out according to Shipp et al. 2009 using Malonate N,N-diphenyl dithiocarbamate 9 (MDP-DTC).

9

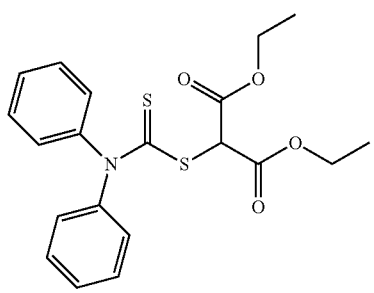

Vidyasagar Malepu et al. "RAFT Polymerization of Vinyl Acetate, Styrene and Acrylates Using N,N-Dithiocarbamates" in *Controlled/Living Radical Polymerization: Progress in RAFT, DT, NMP & OMRP*, Matyjaszewski K, editor; ACS Symposium Series, Vol. 1024, chapter 3, pp 37-47; American Chemical Society, Washington D.C., 2009.

B. Polymer Calculations

Polymer Theoretical Molecular Weight ($M_{n,\,th}$), Moles Monomers, Moles Chain Transfer Agent, Moles Initiator General reaction for synthesis of polymer P from monomers A and B $$A + B \xrightarrow{C,\,I} P$$

A=Hydrophilic Monomer
B=Hydrophobic Monomer
P=Polymer
C=Chain Transfer Agent (CTA)
I=Initiator
Calculation of monomer average molecular weight for polymer P $$[\%A \times MW_A] + [\%B \times MW_B] = \overline{MW}_{AB}$$

% A=percent hydrophilic monomers A in polymer P
% B=percent hydrophobic monomers B in polymer P
$MW_A$=Molecular weight of hydrophilic monomer A
$MW_B$=Molecular weight of hydrophobic monomer B
$\overline{MW}_{AB}$=Average molecular weight of polymer monomers
Calculation of number of monomers in polymer P having a desired (theoretical) molecular weight $M_{n,\,th}$ ($M_n$ in the equation below):

$$M_n / \overline{MW}_{AB} = n_{AB}$$

$n_{AB}$—number of monomers in polymer P having theoretical molecular weight $M_{n,\,th}$
Calculation of moles of monomers A and B in x grams polymer P having theoretical molecular weight $M_{n,\,th}$:

$$\left[\% A \times n_{AB} \times \left(\frac{x}{M_n}\right)\right] = moles_A$$

$$\left[\% B \times n_{AB} \times \left(\frac{x}{M_n}\right)\right] = moles_B$$

$moles_A$=moles hydrophilic monomer A
$moles_B$=moles hydrophobic monomer B
Calculation of moles Chain Transfer Agent for synthesis of x grams polymer P having theoretical molecular weight $M_{n,\,th}$:

$$moles_A/[n_{AB} \times \%A] = moles_B/[n_{AB} \times \%B] = moles_C$$

$moles_C$=moles Chain Transfer Agent
Calculation of moles Initiator for synthesis of x grams polymer P having theoretical molecular weight $M_{n,\,th}$:

$$\%I \times moles_C = moles_I$$

$moles_I$=moles Initiator

C. General Procedure for RAFT Polymerization of Protected Amine Vinyl Ester Random Copolymers CTA and Initiator are combined in a reaction vessel dried under high vacuum. Hydrophilic monomer is added and the mixture is degassed for 1 hour by $N_2$ bubbling. A separate vial of excess hydrophobic monomer is similarly degassed. A measured amount of degassed hydrophobic monomer is added to reaction vessel and the mixture is stirred at 95° C.

overnight. After ~16 hours, the reaction vessel is removed from heat and the solution is allowed to cool to RT. The resulting gel is dissolved in dichloromethane (DCM) and the polymer is precipitated by addition of hexane (~8×vol.). After centrifugation, the solution is decanted and the polymer rinsed with hexane. The rinsed polymer is redissolved in DCM, and precipitated again with hexane (~8×vol.). After centrifugation, the solution is decanted and the polymer dried under high vacuum.

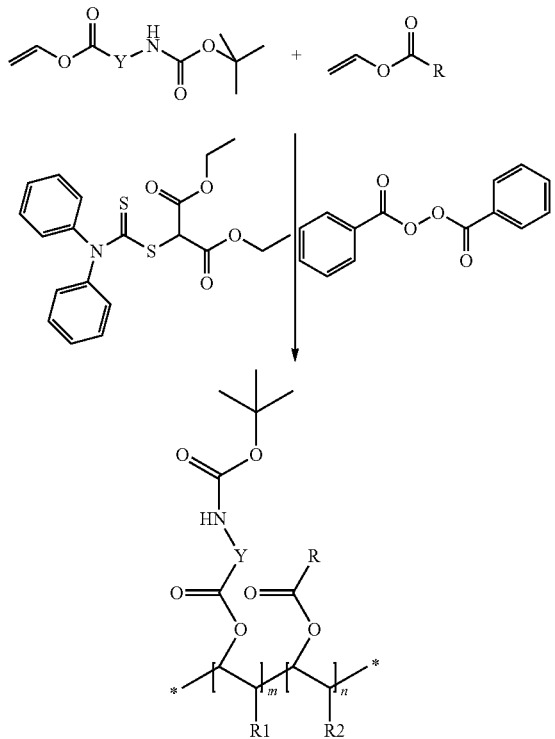

D. NMR Analysis

A sample of the polymer is prepared at 7.5 mg/ml in CDCl$_3$. A $^1$H-NMR spectrum is taken on the Varian 400 Hz MR instrument with a 2 sec relaxation delay and 32-64 scans. The spectrum is analyzed with manual phasing followed by integral and baseline corrections.

E. MALS (Multi-Angle Light Scattering) Molecular Weight Analysis

A sample of the polymer is brought up at 10 mg/ml in a 0.02 μm Whatman anodisc filtered buffer of DCN, 20% THF, 5% ACN. The solution is then filtered through a 0.1 μm Whatman anotop filter. The samples are run at 0.75 ml/min in the above buffer through a Jordi Gel DVB mixed bed analytical column. The sample is then passed through the HELEOS light scattering detector and the optilab REX RI detector. The data is collected and analyzed using ASTRA V software using a previously determined dn/dc of 0.63 ml/gm. The ASTRA V analysis provides Mw and $M_n$.

Example 3

Synthesis of poly(5-tert-butoxycarbonylaminovaleric vinyl ester-co-vinyl butyrate), P(BAVVE-co-VBu)

A. Amine-protected DAN-41947-106 poly(vinyl ester) random copolymer synthesis

Malonate N,N-diphenyl dithiocarbamate (MDPC, 2.56 mg, 0.0066 mmol) and benzoyl peroxide (BPO, 0.795 mg, 0.00328 mmol) were dried in a reaction vessel and 5-tert-Butoxycarbonylamino-valeric vinyl ester 3 (1.00 g, 4.11 mmol) was added. The mixture was degassed by N$_2$ bubbling for 1 h. A separate vial of vinyl butyrate (VBu) was similarly degassed. VBu (345 μL, 2.74 mmol, CAS 123-20-6) was added to the reaction vessel and the mixture was stirred overnight at 95° C. After ~16 h, the reaction vessel was removed from heat and the solution was allowed to cool to room temperature (RT). The resulting gel was dissolved in 5 ml, DCM and the polymer was precipitated by addition of 40 mL hexane. After centrifugation, the solution was decanted and the polymer was rinsed with 5 mL hexane. The rinsed polymer was redissolved in 5 mL DCM, and precipitated again with 40 mL hexane. After centrifugation, the solution was decanted and the polymer was dried under high vacuum. $^1$H NMR (CDCl$_3$): δ 7.4, 4.7-5.25, 3.1, 2.15-2.4, 1.45-1.95, 0.95.

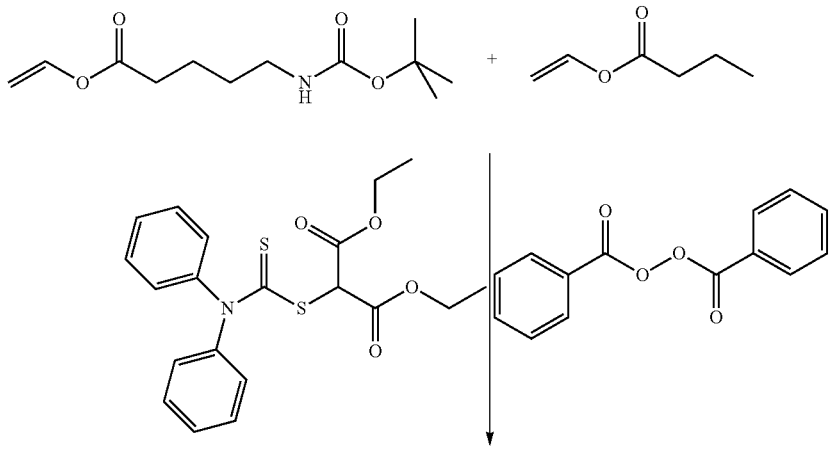

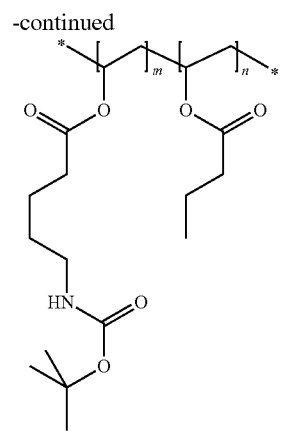

B. Precipitation of Polymer

After drying, the polymer was dissolved in DCM to a concentration of 100 mg/mL and fully or fractionally precipitated by addition of hexane.

Full Precipitation and Fractional Precipitation of (Co) Polymers.

After polymerization, the reaction solution was allowed to cool to room temperature and transferred to a 50 mL centrifuge tube. DCM (2 mL) was used to wash out the reaction vessel and help transfer the reaction solution before hexane (35 mL) was added to the solution. The solution was centrifuged for 2 min at 4,400 rpm. The supernatant layer was carefully decanted and the bottom (viscous liquid or solid) layer was rinsed with hexane. The bottom layer was re-dissolved in DCM (7 mL), precipitated in hexane (35 mL), and centrifuged once more. The supernatant was decanted and the bottom layer rinsed with hexane before the polymer was dried under reduced pressure for several hours.

Fractional Precipitation of (Co)Polymers.

After polymerization, the reaction solution was allowed to cool to room temperature and transferred to a 50 mL centrifuge tube. DCM (2 mL) was used to wash out the reaction vessel and help transfer the reaction solution before hexane (35 mL) was added to the solution. The solution was centrifuged for 2 min at 4,400 rpm. The supernatant layer was carefully decanted and the bottom (viscous liquid or solid) layer was rinsed with hexane. The bottom layer was re-dissolved in DCM (100 mg/mL polymer) before hexane was added. In this case, enough hexane to precipitate half of the total polymer was added—typically, the amount of hexane required to take the solution just past the cloud point. The amount of hexane added to reach this point varied depending on the type and molecular weight of the copolymer solution. The cloudy mixture was centrifuged (3 min at 4,400 rpm), forming two liquid layers. The thicker bottom layer was removed using a glass pipette, diluted with DCM (5 mL), and fully precipitated by adding hexane (30 mL) to yield fraction 1. Hexane was added to the top layer to make a total volume of 50 mL and fully precipitate fraction 2. Both precipitates were centrifuged (2 min at 4,400 rpm), and the fractions recovered by decanting the supernatant, rinsing the precipitated polymer with hexane, and finally dried under reduced pressure for several hours.

C. Polymer Deprotection

Dried polymer was dissolved in 5-10 mL of 2 M HCl in acetic acid solution and stirred at RT for 1 hour. The reaction mixture was diluted with 40 mL deionized $H_2O$ ($dH_2O$), placed in a dialysis bag with nominal MWCO of ~3500 and dialyzed twice for 8-16 hours in high salt (NaCl) and twice for 8-16 hours in $dH_2O$. The polymer was then lyophilized.

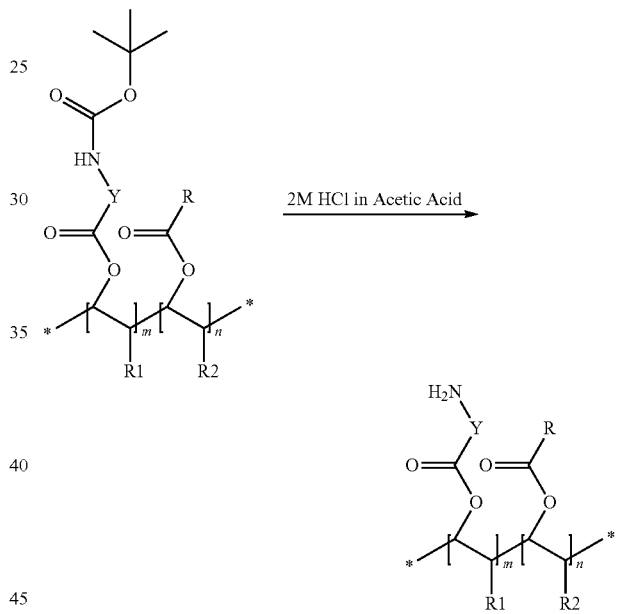

Similar procedures were followed for the copolymerization of BAVVE with VAc, VPr, VBu, or VV. In some cases, 0-3 mL butyl acetate was added to the reaction mixture prior to degassing. The relative concentration of MDPD, initiator, and monomers were altered.

TABLE 1

Exemplary BAVVE-based poly(vinyl ester) copolymers.

| polymer | hydrophobic monomer | monomer feed ratio | $M_{n,\,th}$ | measured PDI |
|---|---|---|---|---|
| DAN-41947-109 | propionyl | 60/40 | 100K | |
| DAN-41947-110 | | | 200K | |
| DAN-41947-107 | | 70/30 | 100K | |
| DAN-41947-108 | | | 200K | |
| DAN-42435-15-A-1 | butyryl | 56:44 | 200K | |
| DAN-41947-47-A-1 | | 60/40 | 30K | 1.23 |
| DAN-41947-47-B-1 | | | 50K | 1.27 |
| DAN-41947-47-C-1 | | | 75K | 1.44 |
| DAN-41947-47-D-1 | | | 100K | 1.51 |
| DAN-41947-47-E-1 | | | 150K | 1.63 |

TABLE 1-continued

Exemplary BAVVE-based poly(vinyl ester) copolymers.

| polymer | hydrophobic monomer | monomer feed ratio | $M_{n, th}$ | measured PDI |
|---|---|---|---|---|
| DAN-41947-105 | | | 100K | |
| DAN-41947-106 or | | | 200K | |
| DAN-41947-129 A | | | | |
| DAN-41947-103 | | 70/30 | 100K | |
| DAN-41947-104 | | | 200K | |
| DAN-42435-14-B-1 | | 75:25 | 200K | |
| DAN-42435-14-A-1 | | 80:20 | 200K | |
| DAN-41947-123 A | valeryl | 60/40 | 100K | |
| DAN-41947-123 B | | | 200K | |
| DAN-41947-122 A | | 70/30 | 100K | |
| DAN-41947-122 B | | | 200K | |
| DAN-42435-78-A-1 | hexanyl | 60:40 | 200K | |
| DAN-42435-80-A-1 | octanyl | 60:40 | 200K | |

Example 4

Synthesis of poly(5-tert-butoxycarbonylaminoproprionic vinyl ester-co-vinylbutyrate), P(BAPVE-co-VBu)

A solution of malonate N,N-diphenyl dithiocarbamate (MDPD, 0.00876 g, 0.0217 mmol), AIBN (0.89 mg, 0.00542 mmol), BAPVE (0.800 g, 0.00374 mol), and butyl acetate (BuAc, 1 mL) were added to a 20 ml vial and degassed by $N_2$ bubbling for 1 h. A separate vial of vinyl butyrate (VBu) was similarly degassed prior to addition via syringe (0.316 mL, 0.00249 mmol). The mixture was stirred for 4 h at 80° C. and then allowed to cool to RT. The resulting viscous solution was dissolved in 5 mL DCM and the polymer was precipitated by addition of 40 mL hexane. After centrifugation, the upper solvent was decanted and the polymer was rinsed with 5 mL hexane. The rinsed polymer was re-dissolved in 5 mL DCM, and precipitated once more with 40 mL hexane. After centrifugation, the upper solvent layer was decanted and the polymer was dried under high vacuum. $^1$H NMR (CDCl$_3$): δ 7.4, 5.3-5.6, 4.7-5.1, 3.35, 2.5, 2.25, 1.55-1.9, 1.45, 0.95. $^{13}$C NMR (CDCl$_3$): δ 171.5, 170.5, 155, 79, 66-68.5, 39-41.5, 37, 35.5, 29.5, 19.5, 15. $M_n$ 27,400 ($M_w/M_n$ 1.34). Yield 74%.

TABLE 2

Exemplary BAPVE-based poly(vinyl ester) copolymers

| polymer | hydro-phobic monomer | monomer feed ratio | incorpo-ration ratio | PDI | Mn |
|---|---|---|---|---|---|
| 32A | acetyl | 60:40 | 60:40 | 1.52 | 29.8K |
| 32C | | 60:40 | 65:35 | 1.51 | 24.6K |
| 32D | | 70:30 | 39:31 | 1.56 | 28.8K |
| 38A | propionyl | 60:40 | 66:34 | 1.47 | 21.6K |
| 38B | | 40:30 | 73:27 | 1.49 | 23.8K |
| DAN-42435-16-B-1 | butyryl | 60:40 | | | 200K$^a$ |
| DAN-42435-16-A-1 | | 70:30 | | | 200K$^a$ |
| 3C | | 60:40 | 63:37 | 1.44 | 29.0K |
| 33A | valeryl | 60:40 | 68:32 | 1.57 | 24.5K |
| 33B | | 60:40 | 62:38 | 1.45 | 23.8K |

$^a M_{n, th}$

Similar procedures were followed for all copolymerizations of BAPVE with VAc, VPr, VBu, or VV. In some cases, 0-3 mL BuAc was added to the reaction mixture prior to degassing, while alternative initiators such as BPO and ADMV were also used. The relative concentration of MDPD, initiator, and monomers were altered.

Example 5

Synthesis of poly(4-tert-butoxycarbonylaminobutyric vinyl ester-co-vinyl butyrate), P(BABVE-co-VBu)

THF solutions of malonate N,N-diphenyl dithiocarbamate (MDPD, 2.56 mg, 0.00634 mmol) and benzoyl peroxide (0.767 mg, 0.00317 mmol) were added to a 20 ml, vial and dried under vacuum for 30 min before BABVE (0.800 mg, 0.00351 mol) was added. The mixture was degassed by $N_2$ bubbling for 1 h. A separate vial of vinyl butyrate was similarly degassed. The vinyl butyrate (296 μL, 0.00234 mol) was added to the reaction vessel and the mixture was stirred overnight at 95° C. After 16 h, the reaction vessel was removed from heat and the solution was allowed to cool to RT. The resulting gel was dissolved in 5 mL DCM and the polymer was precipitated by addition of 40 mL hexane. After centrifugation, the solution was decanted and the polymer was rinsed with 5 mL hexane. The rinsed polymer was redissolved in 5 mL DCM and precipitated once more with 40 mL hexane. After centrifugation, the solution was decanted and the polymer was dried under high vacuum. $^1$H NMR (CDCl$_3$): δ 7.4, 5.05-5.45, 4.7-5.05, 3.15, 2.15-2.45, 1.55-1.9, 1.45, 0.95.

Similar procedures were followed for the copolymerization of BAPVE with VAc, VPr, VBu, or VV. In some cases, 0-3 mL butyl acetate was added to the reaction mixture prior to degassing. The relative concentration of MDPD, initiator, and monomers were altered.

TABLE 3

Exemplary BABVE-based poly(vinylester) copolymers.

| polymer | amine monomer | hydrophobic monomer | monomer feed ratio | $M_{n, th}$ |
|---|---|---|---|---|
| DAN-41947-90 | butyric | butyryl | 50/50 | 100K |
| DAN-41947-93 | | | 60/40 | 100K |
| DAN-41947-96 | | | | 200K |
| DAN-41947-89 | | | 70/30 | 100K |
| DAN-41947-95 | | | | 200K |
| DAN-41947-115 A | | propionyl | 60/40 | 100K |
| DAN-41947-115 B | | | | 200K |
| DAN-41947-114 A | | | 70/30 | 100K |
| DAN-41947-114 B | | | | 200K |
| DAN-41947-119 A | | valeryl | 60/40 | 100K |
| DAN-41947-119 B | | | | 200K |
| DAN-41947-118 A | | | 70/30 | 100K |
| DAN-41947-118 B | | | | 200K |

Example 6

Synthesis of poly 3-(2-tert-butoxycarbonylaminoethoxy)propionic vinyl ester-co-vinyl butyrate), P(BEPVE-co-VBu)

A solution of malonate N,N-diphenyl dithiocarbamate (MDPD, 2.14 mg, 0.0134 mmol), azobisisobutyronitrile (AIBN, 1.09 mg, 0.00665 mmol), and BEPVE (505 mg, 0.00214 mol) were added to a 20 mL vial and degassed by $N_2$ bubbling for 1 h. A separate vial of vinyl butyrate was similarly degassed. The vinyl butyrate (162 mg, 0.00143 mol) was added to the reaction vessel and the mixture was stirred overnight at 95° C. After 16 h, the reaction vessel was removed from heat and the solution was allowed to cool to RT. The resulting viscous solution was dissolved in 5 mL DCM and the polymer was precipitated by addition of 40 mL hexane. After centrifugation, the solution was decanted and the polymer was rinsed with 5 mL hexane. The rinsed polymer was re-dissolved in 5 mL DCM and precipitated once more with 40 mL hexane. After centrifugation, the solution was decanted and the polymer was dried under high vacuum. $^1$H NMR (CDCl$_3$): δ 7.4, 5.1-5.5, 4.75-5.1, 3.65, 3.5, 3.28, 2.55, 2.25, 1.55-1.9, 1.45, 0.95. $^{13}$C NMR (CDCl$_3$): δ 171.5, 169.5, 155, 79, 70.5, 66.5, 41, 40, 37, 35.5, 29.5, 19.5, 15. Mn 23,100 (WM, 1.33). Yield 64%.

Similar procedures were followed for the copolymerization of BEPVE with VAc, VPr, VBu, or VV. In some cases, 0-3 mL butyl acetate was added to the reaction mixture prior to degassing. The relative concentration of MDPD, initiator, and monomers were altered.

Example 7

Masking Agents

A. Galactose Disubstituted Maleic Anhydride Masking Agents

1) Compound 10

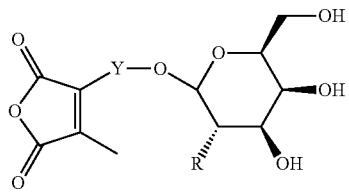

wherein
Y is neutral linker such as, but not limited to:
—(CH$_2$)a-(O—CH$_2$—CH$_2$)$_b$—NH—CO—(CH$_2$)$_c$—, wherein a, b and c are independently integers from 1-6, and
R is a galactose derivative having affinity for the asialoglycoprotein receptor selected from the list comprising:
OH (Galactose),
NH$_2$ (D-Galactosamine),
NH—CO—H (N-formyl-D-galactosamine),
NH—CO—CH$_3$ (N-acetyl-D-galactosamine (GalNAc)),
NH—CO—CH$_2$CH$_3$ (N-propionyl-D-galactosamine),
NH—CO—CH$_2$CH$_2$CH$_3$ (N-n-butanoyl-D-galactosamine), and
NH—CO—CH(CH$_3$)$_2$ (N-iso-butanoyl-D-galactosamine).

Reaction of the maleic anhydride with an anime group on the polymer results in formation of a pH labile linkage between the galactose and a polymer amine.

2) Compound 11

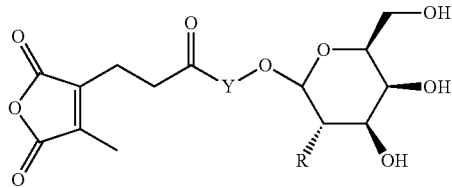

wherein
Y is neutral linker such as, but not limited to:
—NH—(CH$_2$—CH$_2$—O)$_b$—(CH$_2$)$_a$—, wherein b and c are independently integers from 1-6, and
R is as defined above for compound 10.

3) Compound 12

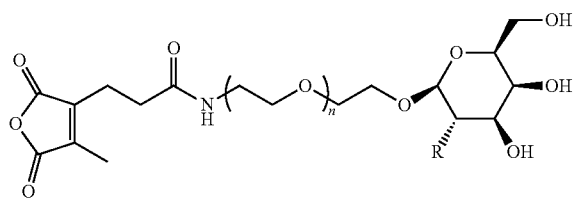

wherein n is an integer from 1 to 6 and R is as defined above for compound 10.

4) Compound 13: N-Acetyl-galactosamine-PEG-methyl maleic anhydride

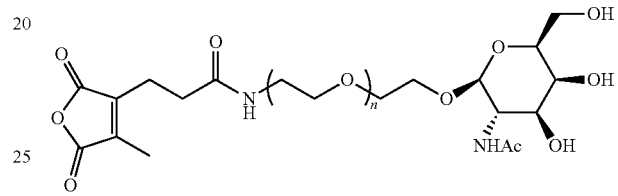

wherein n is an integer from 1 to 6.

5) Alkyl spacer groups may also be used as illustrated in compound 14.

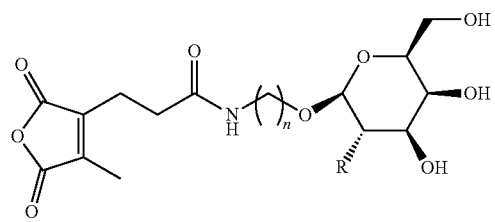

wherein n is an integer from 0 to 10 and R is a defined above for compound 10.

B. Polyethylene Glycol Disubstituted Maleic Anhydride Masking Agents

1) Compound 15

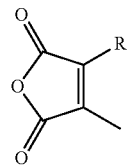

wherein R is neutral and comprises a polyethylene glycol.

Reaction of the maleic anhydride with an anime group on the polymers results in formation of a pH labile linkage between the PEG and a polymer amine.

2) Compound 16

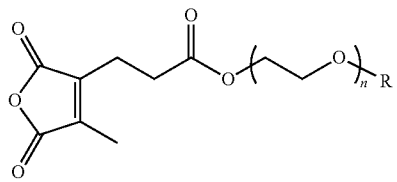

wherein
n is an integer from 1 to 500, and
R is selected from the group consisting of —H, —CH₃, and —CH₂—CH₃.

Preferably, n is an integer from 2 to 100. More preferably, the PEG contains from 5 to 20 ethylene units (n is an integer from 5 to 20). More preferably, PEG contains 10-14 ethylene units (n is an integer from 10 to 14). The PEG may be of variable length and have a mean length of 5-20 or 10-14 ethylene units. Alternatively, the PEG may be monodisperse, uniform or discrete; having, for example, exactly 11 or 13 ethylene units.

C. Dipeptide Masking Agent, Compound 16

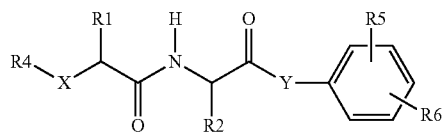

R1 and R2 are the R groups of amino acids,
R4 is a targeting ligand of a steric stabilizer,
X is —NH—, —O—, or —CH₂—,
Y is —NH— or —O—
R5 is at position 2, 4, or 6 and is —CH2-O—C(O)—O—Z wherein Z carbonate, and
R6 is independently hydrogen, alkyl, or halide at each of positions 2, 3, 4, 5, or 6 except for the position occupied by R5.

Example 8

Conjugation of siRNA to Poly(Vinyl Ester) Random Copolymers Via Disulfide Bonds

Disulfide bonds can be made with varying kinetics of cleavage in the reducing environment in a typical mammalian cell.

A. SATA/SMPT Linkage

N-succinimidyl-S-acetylthioacetate (SATA)-modified polynucleotides were synthesized by reaction of 5' amine-modified siRNA with 1 weight equivalents (wt. eq.) of SATA reagent (Pierce) and 0.36 wt. eq. of NaHCO₃ in water at 4° C. for 16 h. The protected thiol modified siRNAs were precipitated by the addition of 9 volumes of ethanol and incubated at −78° C. for 2 h. The precipitate was isolated, dissolved in 1× siRNA buffer (Dharmacon), and quantitated by measuring the absorbance at the 260 nm wavelength.

Separately, polymer in 5 mM TAPS, pH 9, was modified by addition of 1.5 wt % 4-succinimidyloxycarbonyl-α-methyl-α-[2-pyridyldithio]-toluene (SMPT, Pierce). 1 h after addition of SMPT, the SMPT-polymer was added to isotonic glucose solution containing 5 mM TAPS pH 9. To this solution the SATA-modified siRNA was added. The resulting polynucleotide-polymer conjugating disulfide bond is reversible in the reducing environment of the cytoplasm.

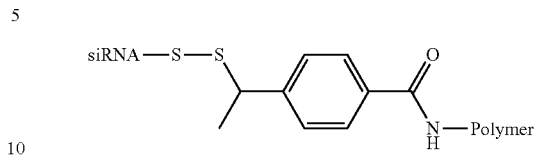

The siRNA-polymer conjugate was then masked by adding HEPES free base to the solution followed by a mixture of CDM-NAG and/or CDM-PEG. The solution was then incubated for 1 h at room temperature (RT) before injection.

B. SATA/SPDP Linkage siRNA having a 5'-amino group on the sense strand was reacted with SATA in the presence of HEPES base pH 7.5. Separately, polymer was reacted with 3-(2-pyridyldithio) propionic acid N-hydroxysuccinimide ester (SPDP) in the presence of HEPES pH 7.5. The modified siRNA and modified polymer were then combined to allow covalent attachment of the siRNA to the polymer.

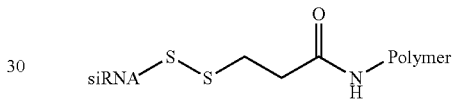

C. 5-methyl-2-iminothiolane linkage siRNA having an strand terminal amino group is reacted with S-acetyl groups to yield siRNA-SAc. The polymer is reacted with 5-methyl-2-iminothiolane (M2IT) in the presence of 5,5'-dithio-bis-(2-nitrobenzoic acid) (DTNB) to yield the polymer having an activated disulfide.

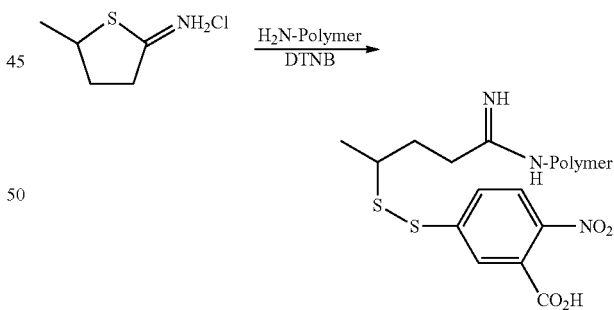

The above modified polymer is then reacted with siRNA-SAc to form the siRNA-polymer conjugate.

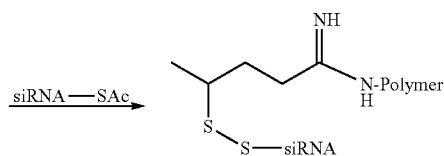

C. Maleic Anhydride Linkage siRNA having a strand terminal amino group is reacted with a disubstituted maleic anhydride derivative, such as a 2-propionic-3-methylmaleic anhydride, that also contains an additional amine reactive group, e.g. CDM-thioester, in the presence alkaline buffer (e.g., HEPES, pH 7.9). To the siRNA-maleic anhydride is added the poly(vinyl ester). The maleic anhydride then reacts with amines on the polymer.

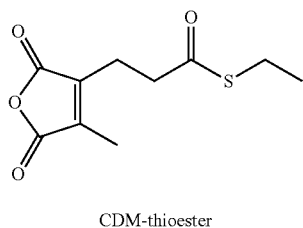

CDM-thioester

Example 9

Reversible Modification (Masking) of Membrane Active Poly(Vinyl Ester) Random Copolymers A. Modification with maleic anhydride-based masking agents. Prior to modification, 5-7×mg of disubstituted maleic anhydride masking agent (e.g. CDM-NAG) was lyophilized from a 0.1% aqueous solution of glacial acetic acid. To the dried disubstituted maleic anhydride masking agent was added a solution of ×mg polymer in 0.2×mL of isotonic glucose and 10×mg of HEPES free base. Following complete dissolution of anhydride, the solution was incubated for at least 30 min at RT prior to animal administration. Reaction of disubstituted maleic anhydride masking agent with the polymer yielded:

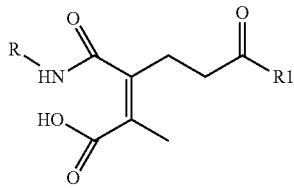

wherein R is poly(vinyl ester) polymer and R1 comprises a targeting ligand or steric stabilizer. The anhydride carboxyl produced in the reaction between the anhydride and the polymer amine exhibits ~$1/20^{th}$ of the expected charge (Rozema et al. Bioconjugate Chemistry 2003). Therefore, the membrane active polymer is effectively neutralized rather than being converted to a highly negatively charged polyanion.

In some applications, the polymer was modified in a two-step process. First CDM-based masking agents with shielding (PEG) and targeting groups were mixed in a ratio of 2:1 (wt:wt) shielding to targeting agent. The polymer was modified with 2×mg of the CDM masking agents mixture for 30 min, followed by attachment of siRNA. The polymer-siRNA conjugate was then further modified with 5×mg of the CDM masking agents mixture. The solution was then incubated at least 1 h at room temperature (RT) before injection into animals.

B. Modification with protease cleavable masking agents. Activated (amine reactive) carbonates of p-acylamidobenzyl alcohol derivatives are reacted with amino groups of amphipathic membrane active polyamines in $H_2O$ at pH>8 to yield a p-acylamidobenzyl carbamate.

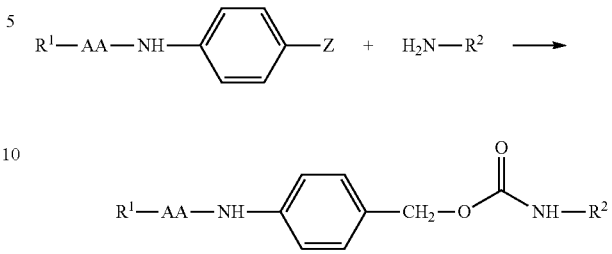

$R^1$ comprises an targeting group ligand (either protected or unprotected) or a PEG, $R^2$ is an amphipathic membrane active poly(vinyl ester), AA is a dipeptide (either protected or unprotected), and Z is an amine-reactive carbonate.

To ×mg polymer was added 10-12×mg of HEPES free base in isotonic glucose. To the buffered polymer solution was added 2× to 16×mg 200 mg/ml dipeptide masking agent in DMF. In some applications, the polymer was modified with 2×mg dipeptide masking agent followed by attachment of siRNA. The polymer-siRNA conjugate was then further modified with 6× to 8×mg dipeptide masking agent. The solution was then incubated at least 1 h at room temperature (RT) before injection into animals. In some applications, the polymer was modified with 2×mg PEG dipeptide masking agent followed by attachment of siRNA. The polymer-siRNA conjugate was then further modified with 6× to 8×mg targeting ligand dipeptide masking agent. The solution was then incubated at least 1 h at room temperature (RT) before injection into animals.

In some applications, the polymer was modified with 2×mg dipeptide masking agent followed by attachment of siRNA. The polymer-siRNA conjugate was then further modified with 6× to 8×mg CDM-based masking agent. The solution was then incubated at least 1 h at RT before injection into animals. In some applications, the polymer was modified with 2×mg PEG dipeptide masking agent followed by attachment of siRNA. The polymer-siRNA conjugate was then further modified with 6× to 8×mg targeting ligand CDM-based masking agent. The solution was then incubated at least 1 h at room temperature (RT) before injection into animals.

Example 10

Conjugate Formation—Masking and Polynucleotide Attachment

A) Polymer was modified with SMPT. After 1 h, 2 wt. equivalents of CDM-NAG (N-acetylgalactoseamine) and/or CDM-PEG (average 11 units) was added to the polymer in the presence of HEPES base. To this solution was added SATA-siRNA. After overnight incubation, CDM-NAG and/or CDM-PEG was added to the conjugate.

B) Polymer was modified with SMPT. After 1 h, 2 wt equivalents of PheCit-NAG (N-acetylgalactoseamine) and/or PheCit-PEG (average 11 unites) was added to the polymer in the presence of HEPES base. To this solution was added SATA-siRNA. After overnight incubation, a PheCit-NAG and/or PheCit-PEG was added to the conjugate.

Example 10 siRNAs

The siRNAs had the following sequences:
Factor VII—Rodent

```
sense:
                                        (SEQ ID 1)
5' GfcAfaAfgGfcGfuGfcCfaAfcUfcAf(invdT) 3' antisense:
                                        (SEQ ID 2)
5' pdTsGfaGfuUfgGfcAfcGfcCfuUfuGfcdTsdT 3'
or sense
                                        (SEQ ID 3)
5' GGAUfcCfAUfCtUfCfAAGUfCfUfUfACfdTsdT 3' antisense
                                        (SEQ ID 4)
5' GUfAAGACfUfUfGAGAUfGAUfCfCfdTsdT 3'
```

Factor VII=Primate

```
Sense
                                        (SEQ ID 5)
5' uuAGGfuUfgGfuGfaAfuGfgAfgCfuCfaGf(invdT) 3'

Antisense
                                        (SEQ ID 6)
5' pCfsUfgAfgCfuCfcAfuUfcAfcCfaAfcdTsdT 3'
```

ApoB siRNA:

```
sense
                                        (SEQ ID 7)
5' GGAAUCuuAuAuuuGAUCcAsA 3' antisense
                                        (SEQ ID 8)
5' uuGGAUcAAAuAuAAGAuUCcscsU 3'
``` siLUC

```
sense
                                        (SEQ ID 9)
5'-uAuCfuUfaCfgCfuGfaGfuAfcUfuCfgAf(invdT)-3' antisense
                                        (SEQ ID 10)
5'-UfcGfaAfgUfaCfuCfaGfcGfuAfaGfdTsdT-3'
``` lower case=2'-O—CH$_3$ substitution
s=phosphorothioate linkage
f after nucleotide=2'-F substitution
d before nucleotide=2'-deoxy RNA synthesis was performed on solid phase by conventional phosphoramidite chemistry on an ÄKTA Oligopilot 100 (GE Healthcare, Freiburg, Germany) with controlled pore glass (CPG) as solid support.

Example 11

Synthesis of Amino-Modified RNA

RNA equipped with a C-6-aminolinker at the 5'-end of the sense strand was produced by standard phosphoramidite chemistry on solid phase at a scale of 1215 μmol using an ÄKTA Oligopilot 100 (GE Healthcare, Freiburg, Germany) and controlled pore glass as solid support (Prime Synthesis, Aston, Pa., USA). RNA containing 2'-O-methyl nucleotides were generated employing the corresponding phosphoramidites, 2'-O-methyl phosphoramidites, and TFA-hexylaminolinker amidite (Sigma-Aldrich, SAFC, Hamburg, Germany). Cleavage and deprotection as well as purification was achieved by methods known in the field (Wincott F., et al, NAR 1995, 23, 14, 2677-84).

Example 12

In Vivo Delivery of RNAi Polynucleotides Using Poly(Vinyl Ester) Delivery Polymers RNAi polynucleotide conjugates and masked poly(vinyl ester) polymers were synthesized as described above. Six to eight week old mice (strain C57BL/6 or ICR, ~18-20 g each) were obtained from Harlan Sprague Dawley (Indianapolis, Ind.). Mice were housed at least two days prior to injection. Feeding was performed ad libitum with Harlan Teklad Rodent Diet (Harlan, Madison Wis.). Mice were injected by infusion into the tail vein with 0.4 mL solution of delivery polymer-siRNA conjugates into the tail vein unless stated otherwise. The composition was soluble and nonaggregating in physiological conditions. Injection into other vessels, e.g. retro-orbital injection, are predicted to be equally effective.

Wistar Han rats, 175-200 g were obtained from Charles River (Wilmington, Mass.). Rats were housed at least one (1) week prior to injection. Injection volume for rats was typically 1 ml.

The indicated amount of polymer-siRNA conjugate was administered to Cynomolgus macaque (*Macaca fascicularis*) primates (male, 3.0 to 8.0 kg) via injection into the saphenous vein using a 22 to 25 gauge intravenous catheter. As a control, another set of primates were injected with isotonic glucose. Blood tests for blood urea nitrogen (BUN), alanine transaminase (ALT), aspartate aminotransferase (AST), and creatinine were performed on a Cobas Integra 400 (Roche Diagnostics) according to the manufacturer's recommendations.

Mice, rats, and primates were fasted for 4 h, 16 h, or overnight, before injection. Primates were fasted overnight before blood collection or tissue harvest. Blood samples were collected by submandibular bleeding for mice, from jugular vein for rats, and from femoral vein for primates. For mice and rats, samples were taken 2 days after polymer injection, unless indicated otherwise. For primates, blood samples are collected on day 2 (24 h after injection) and day 4 (72 h after injection). Further, for primates, blood sample collections were carried out up to day 81. Serum for use in Western assays was collected and added to an equal volume of Complete Protease Inhibitor Cocktail containing EDTA (Roche, Indianapolis Ind.) and stored at −20° C. Total RNA was isolated from liver immediately after harvest using TRI-REAGENT® according to the manufacturer's protocol (Molecular Research Center, Cincinnati Ohio).

Serum ApoB Levels Determination.

Serum ApoB protein levels were determined by standard sandwich ELISA methods. Briefly, a polyclonal goat anti-mouse ApoB antibody and a rabbit anti-mouse ApoB antibody (Biodesign International) were used as capture and detection antibodies respectively. An HRP-conjugated goat anti-rabbit IgG antibody (Sigma) was applied afterwards to bind the ApoB/antibody complex. Absorbance of tetramethyl-benzidine (TMB, Sigma) colorimetric development was then measured by a Tecan Safire2 (Austria, Europe) microplate reader at 450 nm.

Plasma Factor VII (F7) Activity Measurements.

Plasma samples from animals were prepared by collecting blood (9 volumes) (by submandibular bleeding for mice or from jugular vein for rats) into microcentrifuge tubes containing 0.109 mol/L sodium citrate anticoagulant (1 volume) following standard procedures. F7 activity in plasma is measured with a chromogenic method using a BIOPHEN VII kit (Hyphen BioMed/Aniara, Mason, Ohio) following manufacturer's recommendations. Absorbance of colorimetric development was measured using a Tecan Safire2 microplate reader at 405 nm.

Example 13

Factor VII Knockdown in Mouse, Rat, and Non-Human Primate Following Factor VII siRNA Delivery by P(BAVVE-Co-VBu) Polymer P(BAVVE-co-VBu) polymer (DAN-41947-106-1 or DAN-41947-129-1) was reversibly modified with 2.3 wt equivalents of CDM-NAG and 4.7 wt equivalents CDM-PEG and conjugated to Factor VII siRNA (duplex of SEQ ID 3 and 4) as described above. Effect on Factor VII levels was determined as described above. Effective knockdown of Factor VII activity was observed using about 0.5 mg/kg to nearly 16 mg/kg P(BAVVE-co-VBu) polymer without causing a more than 3-fold increase in blood urea nitrogen (BUN), alanine transaminase (ALT), aspartate aminotransferase (AST), or creatinine levels.

TABLE 4

Inhibition of Factor VII activity in normal liver cells in animal treated with CDM-NAG/CDM-PEG masked P(BAVVE-co-VBu) polymer conjugated to Factor VII-siRNA.

| | | | % target gene knockdown | | |
|---|---|---|---|---|---|
| polymer | siRNA mg/kg | polymer mg/kg | mouse | rat | non-human primate |
| DAN-41947-106-1 | 2 | 7.5 | 81 | | |
| | | 15 | 100 | | |
| | 0.2 | 0.5 | | 68 | |
| | | 1 | | 87 | |
| | | 5 | | 81 | |
| | | 8 | | 86 | |
| | | 10 | | 91 | |
| | | 12 | | 83 | |
| | | 16 | | 74 | |
| | 0.8 | 12 | | 97 | |
| DAN-41947-129-1 | 0.125 | 0.5 | | | 80 |
| | 0.25 | 1 | | | 97 |
| | 2 | 7.5 | 70 | | |
| | 0.2 | 0.5 | | | 80 |
| | 0.2 | 12 | | | 85 |

Example 14

Target Gene Knockdown in Mouse Following siRNA Delivery Using Poly(Vinyl Ester) Delivery Polymers with Varying Monomer Ratio Composition P(BAVVE-co-VBu) or P(BAPVE-co-VBu) polymers with varying amine monomer:hydrophobic monomer compositions were reversibly modified with 2.3 wt equivalents of CDM-NAG and 4.7 wt equivalents CDM-PEG and conjugated to Factor VII siRNA (duplex of SEQ ID 3 and 4 above) as described above. 7.5 mg/kg polymer and 2 mg/kg siRNA were injected into each mouse. Effect on Factor VII levels were determined as described above. The results demonstrate that effective knockdown was observed with polymers having 56-80% amine content. However, polymers having 56-60% amine content were the most efficient.

TABLE 5 siRNA delivery to normal liver cells in mice treated with masked P(BAVVE-co-VBu) or P(BAPVE-co-VBu) delivery polymers as determined by target gene knockdown.

| polymer | amine monomer | hydrophobic monomer | ratio | $M_{n,th}$ | % target gene knockdown |
|---|---|---|---|---|---|
| DAN-42435-15-A-1 | valeric | butyryl | 56:44 | 200 KDa | 90% |
| DAN-41947-106-1 | valeric | butyryl | 60:40 | 200 KDa | 81% |
| DAN-42435-16-A-1 | propionyl | butyryl | 70:30 | 200 KDa | 70% |
| DAN-42435-14-B-1 | valeric | butyryl | 75:25 | 200 KDa | 60% |
| DAN-42435-14-A-1 | valeric | butyryl | 80:20 | 200 KDa | 40% |

Example 15

Target Gene Knockdown in Mouse Following siRNA Delivery Using Poly(Vinyl Ester) Delivery Polymers Formed with Different Amine Monomers P(BAPVE-co-VBu), P(BABVE-co-VBu), and P(BAVVE-co-VBu) polymers were reversibly modified with 2.3 wt equivalents of CDM-NAG and 4.7 wt equivalents CDM-PEG and conjugated to Factor VII siRNA (duplex of SEQ ID 3 and 4 above) as described above. 7.5 mg/kg polymer and 2 mg/kg siRNA were injected into each mouse. Effect on Factor VII levels was determined as described above. The results demonstrate that effective knockdown was observed with each of the amine monomers tested.

TABLE 6 siRNA delivery to normal liver cells in mice treated with masked P(BAPVE-co-VBu), P(BABVE-co-VBu), and P(BAVVE-co-VBu) delivery polymers as determined by target gene knockdown.

| polymer | amine monomer | hydrophobic monomer | monomer feed ratio | $M_{n,th}$ | % target gene knockdown |
|---|---|---|---|---|---|
| DAN-42435-16-B-1 | propionyl | butyryl | 60:40 | 200 KDa | 90% |
| DAN-41947-96-1 | butyryl | butyryl | 60:40 | 200 kDa | 84% |
| DAN-41947-106-1 | valeric | butyryl | 60:40 | 200 KDa | 81% |

Example 16

Target Gene Knockdown in Mouse Following siRNA Delivery Using Poly(Vinyl Ester) Delivery Polymers with Different Hydrophobic Monomers P(BAVVE-co) polymers with different hydrophobic monomers were reversibly modified with 2.3 wt equivalents of CDM-NAG and 4.7 wt equivalents CDM-PEG and conjugated to Factor VII siRNA (duplex of SEQ ID 3 and 4 above) as described above. 7.5 mg/kg polymer and 2 mg/kg siRNA were injected into each mouse. Effect on Factor VII levels was determined as described above. The results demonstrate that effective knockdown was observed with butyryl and valeryl hydrophobic monomers. Polymers having butyryl hydrophobic monomers were more efficient.

TABLE 7 siRNA delivery to normal liver cells in mice treated with masked P(BAVVE-co-hydrophobic vinyl ester) delivery polymers as determined by target gene knockdown.

| polymer | amine monomer | hydrophobic monomer | % target gene knockdown |
|---|---|---|---|
| DAN-41947-110-1 | valeryl | propionyl (C3) | 0% |
| DAN-41947-106-1 | valeryl | butyryl (C4) | 81% |
| DAN-41947-123-B-1 | valeryl | valeryl (C5) | 30% |
| DAN-42435-82-A-1 | valeryl | valeryl (C5) | 50% |
| DAN-42435-78-A-1 | valeryl | hexanyl (C6) | 0% |
| DAN-42435-80-A-1 | valeryl | octanyl (C8) | 0% |

Example 17

Target Gene Knockdown in Mouse Following siRNA Delivery Using Poly(Vinyl Ester) Delivery Polymers with Varying Molecular Weights P(BAVVE-co-VBu) polymers with varying molecular weights were reversibly modified with 2.3 wt equivalents of CDM-NAG and 4.7 wt equivalents CDM-PEG and conjugated to Factor VII siRNA (duplex of SEQ ID 3 and 4 above) as described above. 7.5 mg/kg polymer and 2 mg/kg siRNA were injected into each mouse. Effect on Factor VII levels was determined as described above. The results demonstrate that effective knockdown was observed with P(BAVVE-co-VBu) polymers having 23 k-200 k $M_{n,\,th}$. Polymers having $M_{n,\,th}$ greater than 67 kDa (70 kDa Mw) were more efficient. Polymers with 100-150 kDa (67-86 kDa Mw) were most preferred.

TABLE 8 siRNA delivery to normal liver cells in mice treated with masked P(BAVVE-co-VBu) delivery polymers with varying molecular weight as determined by target gene knockdown.

| polymer | $M_{n,\,th}$ | Mw | % target gene knockdown |
|---|---|---|---|
| DAN-41947-47-A-1 | 30 kDa | 23150 | 20% |
| DAN-41947-47-B-1 | 50 kDa | 42370 | 50% |
| DAN-41947-47-C-1 | 75 kDa | 67960 | 80% |
| DAN-41947-47-D-1 | 100 kDa | 76600 | 90% |
| DAN-41947-47-E-1 | 150 kDa | 86100 | 90% |
| DAN-41947-106-1 | 200 kDa |  | 81% |

Example 18

Amphipathic Cationic Poly(Vinyl Ester) Random Copolymers are Effective In Vitro Transfection Reagents The indicated copolymer (500 mg) was dissolved in a solution of 2 N HCl in acetic acid (5 mL) and stirred for 1 h. The solution was diluted with water (30 mL) and dialyzed against an aqueous NaCl solution and then deionized water over two days. The solution was then lyophilized and re-dissolved in $H_2O$ to make up 20 mg/mL solutions. Hep3B-SEAP (hepatocellular carcinoma), MCF7 (breast cancer), HT29 (colon cancer), HepG2-SEAP (hepatocellular carcinoma), or A375 (melanoma) cells as indicated were plated in 96-well culture plates at a density of 10,000 cells/well. Cells were transfected with either 1.5 μg/mL or 3 μg/mL of copolymer and 500 ng/mL of Aha1 siRNA prepared in OPTI-MEM reduced-serum medium (Gibco). 24 h post-transfection, the cells were lysed and processed for quantitative real-time PCR (qRT-PCR) using the TaqMan Gene Expression Cells-to-CT Kit (Life Technologies). Biplex qRT-PCR was performed using TaqMan assays for human Aha1 (product # Hs00201602 m1) and human CycA (product #4326316E) on a StepOne Real-Time PCR System (Life Technologies). Analysis was performed using the ΔΔCT method of relative gene expression quantitation.

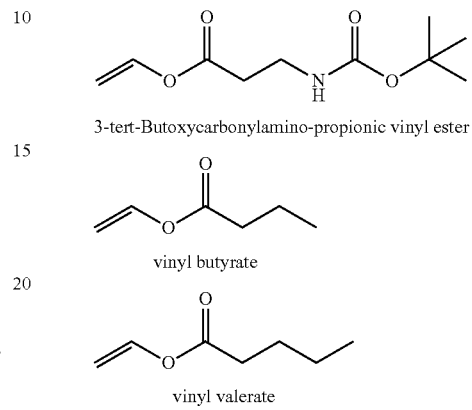

3-tert-Butoxycarbonylamino-propionic vinyl ester vinyl butyrate vinyl valerate

TABLE 9

Poly(vinyl ester) polymers used for in vitro transfection.

| polymer | | % Amine | MW[a] |
|---|---|---|---|
| short name | long name | | |
| BAPVE-VBu | 3-tert-Butoxycarbonylamino-propionic vinyl ester + vinyl butyrate | 50 | 23.9 |
| | | 50 | 57.5 |
| | | 62 | 69.7 |
| | | 63 | 27.0 |
| | | 63 | 67.6 |
| | | 68 | 63.4 |
| | | 71 | 23.3 |
| | | 71 | 59.0 |
| BAPVE-VV | 3-tert-Butoxycarbonylamino-propionic vinyl ester + vinyl valerate | 62 | 17.5 |
| | | 67 | 15.4 |
| | | 78 | 17.2 |
| | | 92 | 50.4 |

[a]kDa

TABLE 10

Knockdown of Aha1 in vitro following Aha1 siRNA by poly(vinyl ester) polymers. Polymers are listed in same order as in Table 9.

| | % Aha1 Knockdown cell type | | | | | | | | | |
|---|---|---|---|---|---|---|---|---|---|---|
| | Hep3B-SEAP | | MCF7 | | HT29 | | HepG2-SEAP | | A375 | |
| polymer dose[a] | 3.0 | 1.5 | 3.0 | 1.5 | 3.0 | 1.5 | 3.0 | 1.5 | 3.0 | 1.5 |
| BAPVE-VBu | 69 | 86 | 33 | 49 | 17 | 9 | 55 | 53 | 68 | 68 |
| | 83 | 90 | 37 | 53 | 14 | 9 | 70 | 58 | 80 | 80 |
| | 52 | 75 | 34 | 23 | 17 | 6 | 34 | 36 | 51 | 66 |
| | 61 | 80 | 33 | 25 | 5 | −7 | 34 | 36 | 56 | 54 |
| | 72 | 74 | 41 | 27 | 9 | −13 | 50 | 49 | 62 | 57 |
| | 55 | 70 | 36 | 19 | 14 | 12 | 39 | 29 | 58 | 40 |
| | 33 | 38 | 36 | 13 | 1 | −8 | 4 | 7 | 33 | 23 |
| | 43 | 31 | 39 | 21 | 8 | −16 | 13 | 15 | 60 | 28 |

TABLE 10-continued

Knockdown of Aha1 in vitro following Aha1 siRNA by poly(vinyl ester) polymers. Polymers are listed in same order as in Table 9.

| | % Aha1 Knockdown cell type | | | | | | | | | |
|---|---|---|---|---|---|---|---|---|---|---|
| | Hep3B-SEAP | | MCF7 | | HT29 | | HepG2-SEAP | | A375 | |
| polymer dose[a] | 3.0 | 1.5 | 3.0 | 1.5 | 3.0 | 1.5 | 3.0 | 1.5 | 3.0 | 1.5 |
| BAPVE-VV | 81 | 90 | 51 | 46 | 17 | 13 | 57 | 68 | 67 | 80 |
| | 41 | 46 | 23 | 15 | 16 | 10 | 27 | 23 | 71 | 69 |
| | 36 | 55 | 22 | 26 | 16 | 12 | 26 | 21 | 71 | 64 |
| | 48 | 76 | 34 | 35 | 29 | 19 | 45 | 40 | 82 | 79 |

[a] μg/mL

Figure 2:
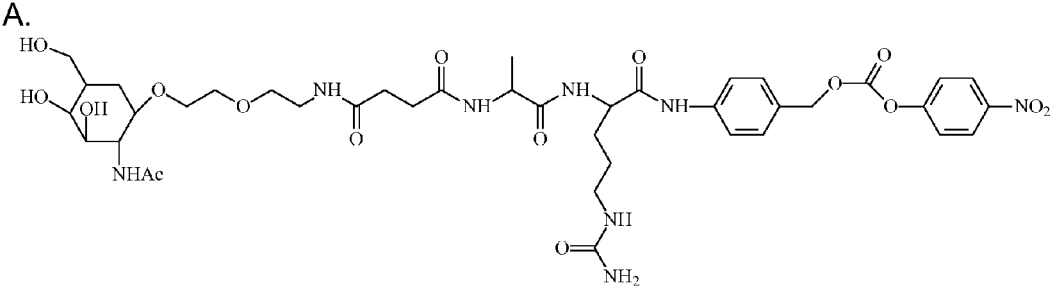
FIG. 2. Illustration showing the structures of various dipeptide masking agents.
Figure 2:
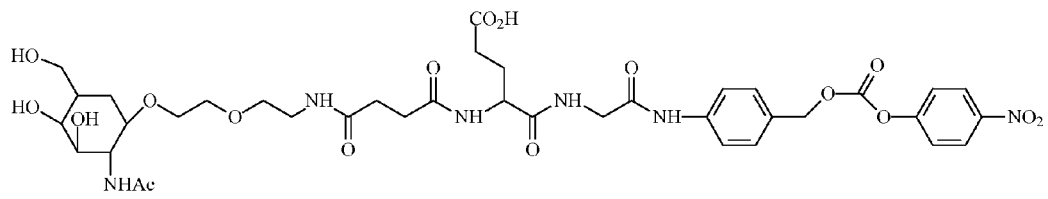
Figure 2:
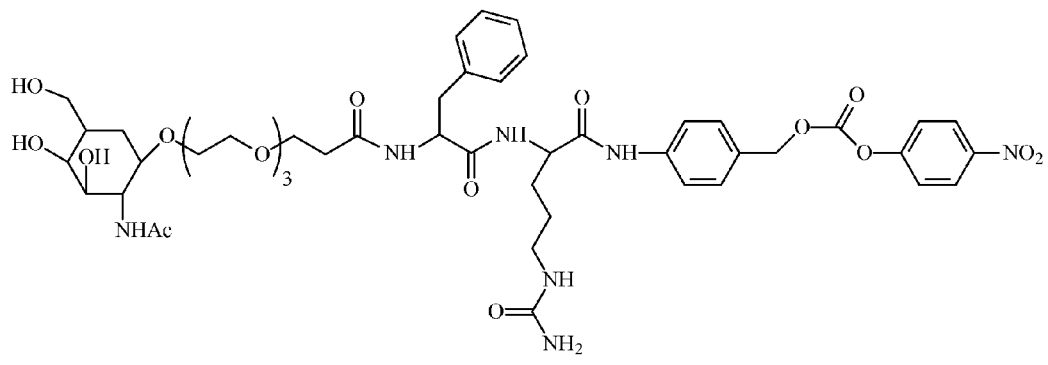
Figure 2:
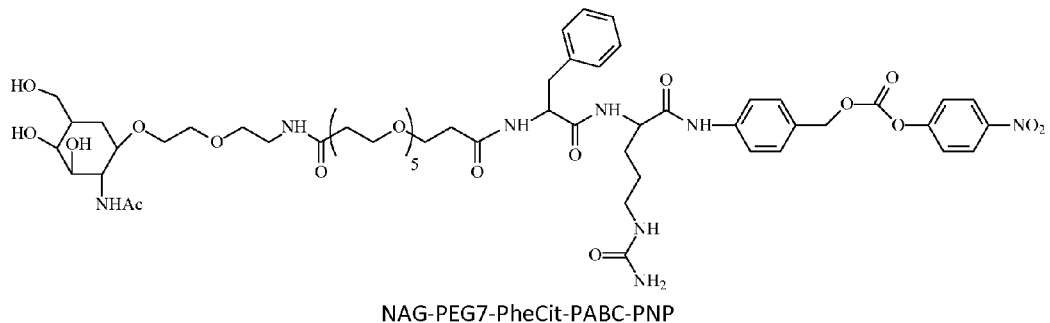
Figure 2:
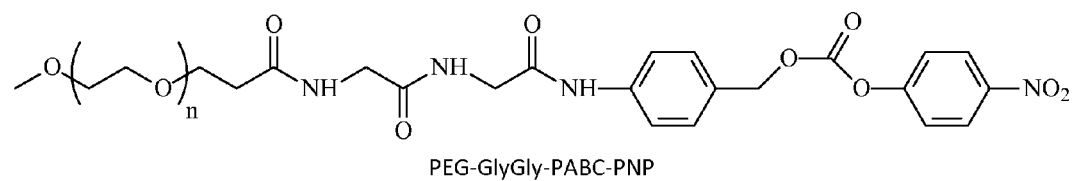
Figure 2:
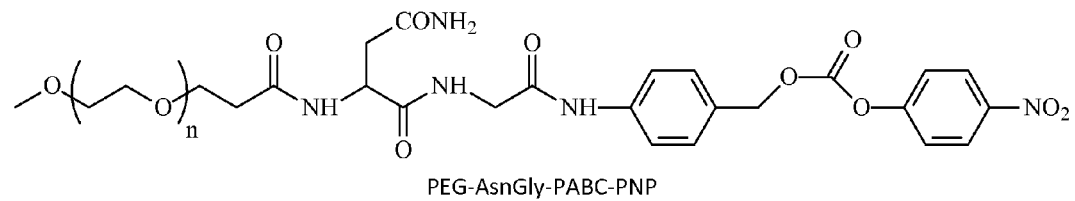
Figure 2:
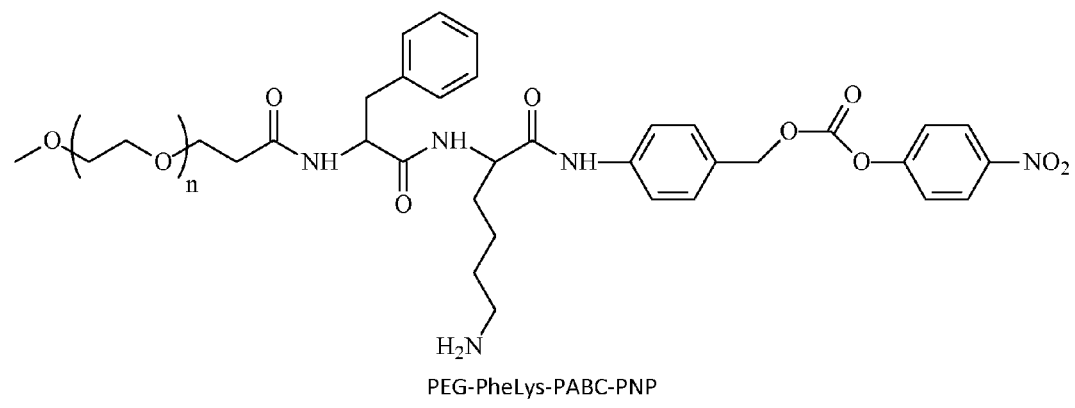
Figure 2:
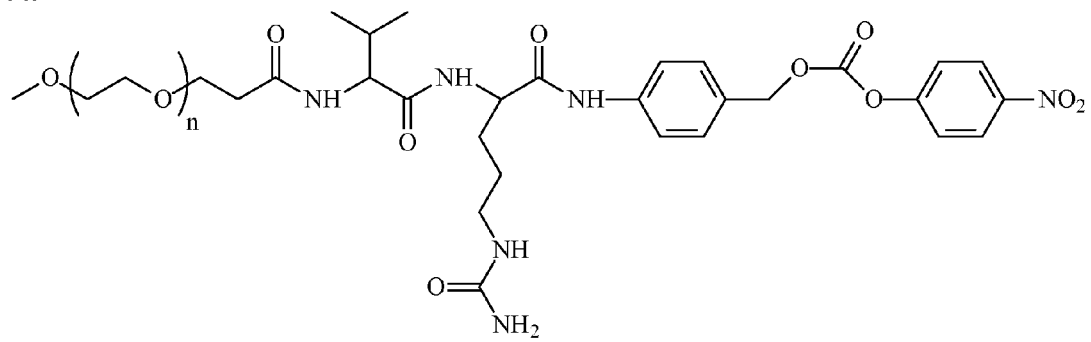
Figure 2:
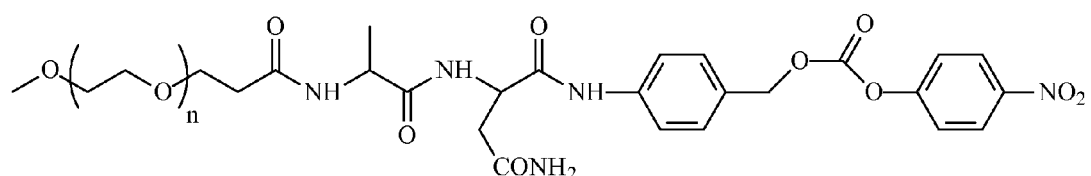
Figure 2:
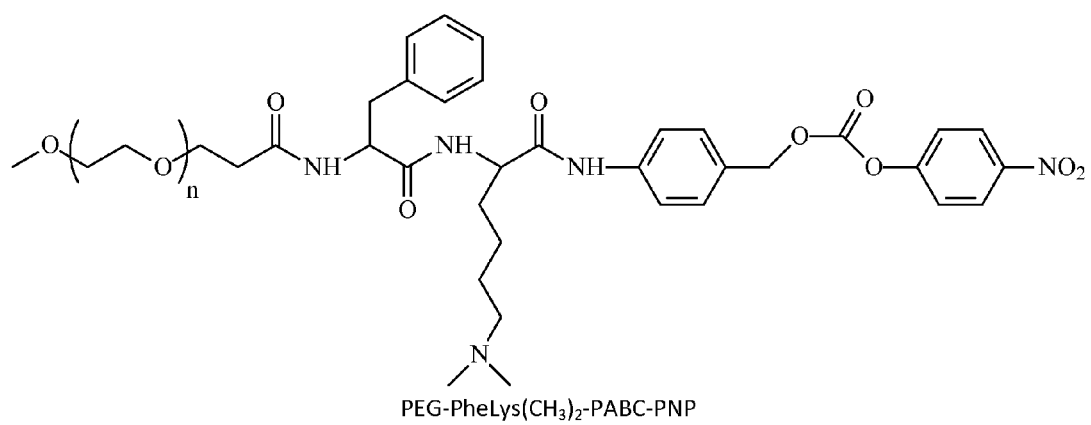
Figure 2:
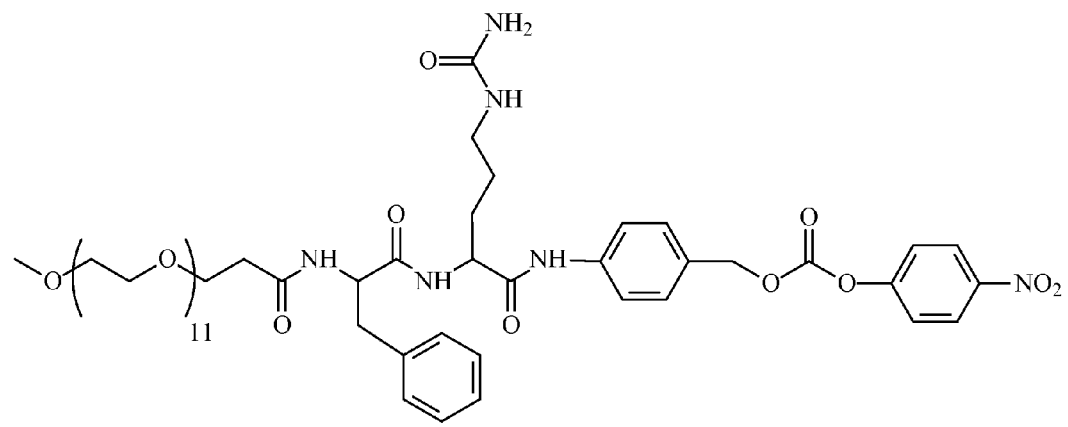

Example 19 siRNA Delivery In Vivo Upon Subcutaneous Injection Using NAG/PEG-AA-p-Nitrophenyl-Carbamate Poly(Vinyl Ester) DPCs Polyvinylester DAN-41947-129-1 in 100 mM pH 7.5 HEPES buffer was modified 0.5 wt % with the activated disulfide reagent succinimidyloxycarbonyl-alpha-methyl-alpha(2-pyridyldithio)toluene (SMPT) from Pierce. The thiol-reactive polymer was diluted to 5 mg/mL in 60 mg/mL HEPES base. To this solution was added 10 mg/mL PEG(12 unit)-Phe-Cit-p-nitrophenyl-carbonate masking reagent. After 1 hour, acetate-protected thiol Factor VII siRNA was added to polymer solution at a polymer to siRNA ratio range of 5-10 to 1. After incubation overnight, NAG-Ala-Cit-p-nitrophenyl-carbamate masking reagent (FIG. 2) was added to 30 mg/mL. After incubation for at least 60 minutes, but no longer than 4 hours, the DPC was injected subcutaneously in the area behind the neck of 20 g ICR mice. At various times after injection, a sample of serum was harvested and the levels of fVII were measured. As a control similarly prepared DAN-41947-129-1-siRNA conjugate was injected intravascularly.

TABLE 11

Knockdown of Factor VII in vivo in mice treated with PEG$_{12}$-Phe-Cit/NAG-Ala-Cit-p-nitrophenyl-carbamate DPCs

| Masking Agent | Days Postinjection | Polymer dose (mg/kg)[a] | siRNA dose (mg/kg)[a] | % fVII activity[b] |
|---|---|---|---|---|
| 2 wt equivalents 12 unit PEG12-PheCit followed by 6 wt NAG-PheCit | 3 | 25 | 2.5 | 3 |
| | 5 | 25 | 2.5 | 2 |
| | 7 | 25 | 2.5 | 2 |
| 2 wt equivalents 12 unit PEG24-PheCit followed by 6 wt NAG-AlaCit | 5 | 25 | 2.5 | 2 |
| I.V. injection control 2 wt equivalents 12 unit PEG14-PheCit followed by 6 wt NAG-AlaCit | 2 | 10 | 0.5 | 27 |

[a] mg polymer or siRNA per kg animal weight
[b] relative to naive control

Example 20

Inhibition of Endogenous Gene Expression in In Vivo Following Co-Administration of Cholesterol-siRNA and Masked Amphipathic Poly(Vinyl Ester) Random Copolymers The poly(vinyl ester) polymer DAN-41947-129-1 were masked by disubstituted maleic anhydride masking agents or didpeptide masking agents as described above. The masked polymers were then co-injected with cholesterol-siRNA (ApoB or Factor VII) into mice and the effect on target gene expression was determined.

TABLE 12

DAN-41947-129-1 (15 mg/kg) masked with CDM-PEG and CDM-NAG or PEG(12)-PheCit and NAG-AlaCit was co-injected with cholesterol conjugate siRNA mice. 48 h after injection, ApoB knockdown was measured.

| masking agent | siRNA gene | siRNA μg | injection volume | % gene activity[a] |
|---|---|---|---|---|
| 4.7 × CDM-PEG 2.3 × CDM-NAG | ApoB | 40 | 200 μL | 1 |
| 2 × PEG(12)-PheCit 6 × NAG-AlaCit | fVII | 100 | 300 μL | 3 |

[a] relative to isotonic glucose injection control

We claim:

1. A membrane active poly(vinyl ester) random copolymer having the structure represented by:

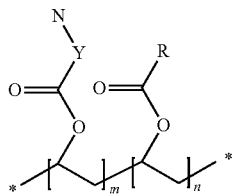

wherein:
N is NH$_2$,
Y is (CH$_2$)$_a$ or (CH$_2$)$_2$—O—(CH$_2$)$_2$ wherein a is 1, 2, or 3,
R is a hydrophobic group having 2-6 carbon atoms,
m and n are independently integers greater than zero (0), the ratio m/n is about 1 to about 4,
the poly(vinyl ester) random copolymer is capable of causing red blood cell lysis,
the polydispersity of the polymer is less than or equal to 1.5, and
the molecular weight of the polymer is about 30 kDa to about 100 kDa.

2. The poly(vinyl ester) random copolymer of claim 1 wherein the polydispersity of the polymer is less than or equal to 1.3.

3. The poly(vinyl ester) random copolymer of claim 1 wherein the molecular weight of the polymer is about 30 kDa to about 50 kDa.

4. The poly(vinyl ester) random copolymer of claim 1 wherein the molecular weight of the polymer is about 50 kDa to about 75 kDa.

5. The poly(vinyl ester) random copolymer of claim 1 wherein the ratio m/n is about 1.

6. The poly(vinyl ester) random copolymer of claim 1 wherein the ratio m/n is about 75/25.

7. The poly(vinyl ester) random copolymer of claim 1 wherein Y is (CH$_2$).

8. The poly(vinyl ester) random copolymer of claim 1 wherein Y is (CH$_2$)$_2$.

9. The poly(vinyl ester) random copolymer of claim 1 wherein Y is (CH$_2$)$_3$.

10. The poly(vinyl ester) random copolymer of claim 1 wherein Y is (CH$_2$)$_2$—O—(CH$_2$)$_2$.

11. The poly(vinyl ester) random copolymer of claim 1 wherein R is a hydrophobic group having 3 carbon atoms.

12. The poly(vinyl ester) random copolymer of claim 11 wherein Y is (CH$_2$)$_3$.

13. The poly(vinyl ester) random copolymer of claim 12 wherein the ratio m/n is about 1.

14. The poly(vinyl ester) random copolymer of claim 12 wherein the ratio m/n is about 3.

15. The poly(vinyl ester) random copolymer of claim 11 wherein Y is (CH$_2$)$_2$—O—(CH$_2$)$_2$.

16. The poly(vinyl ester) random copolymer of claim 15 wherein the ratio m/n is about 1.

17. The poly(vinyl ester) random copolymer of claim 15 wherein the ratio m/n is about 3.

18. The poly(vinyl ester) random copolymer of claim 11 wherein Y is (CH$_2$)$_2$—O—(CH$_2$)$_2$.

19. The poly(vinyl ester) random copolymer of claim 18 wherein the ratio m/n is about 3.

20. The poly(vinyl ester) random copolymer of claim 18 wherein the ratio m/n is about 1.

21. A composition for inhibiting gene expression in vivo comprising the poly(vinyl ester) random copolymer of claim 20 and an RNA interference polynucleotide in a pharmaceutically acceptable carrier.

22. The composition of claim 21 wherein the poly(vinyl ester) random copolymer is conjugated to an RNA interference polynucleotide.

23. The composition of claim 21 wherein the RNA interference polynucleotide is conjugated to a hydrophobic group containing at least 20 carbon atoms.

24. The poly(vinyl ester) random copolymer of claim 1 wherein R is a hydrophobic group having 4 carbon atoms.

25. The poly(vinyl ester) random copolymer of claim 24 wherein the hydrophobic group is branched.

26. The poly(vinyl ester) random copolymer of claim 25 wherein Y is (CH$_2$)$_3$.

27. The poly(vinyl ester) random copolymer of claim 26 wherein the ratio m/n is about 1.

28. The poly(vinyl ester) random copolymer of claim 26 wherein the ratio m/n is about 3.

29. The poly(vinyl ester) random copolymer of claim 1 wherein greater than 50% of N are reversibly modified by reaction with disubstituted maleic anhydride masking agents, dipeptide-amidobenzyl-carbonate masking agents, or a combination of disubstituted maleic anhydride masking agents and dipeptide-amidobenzyl-carbonate masking agents.

30. The poly(vinyl ester) random copolymer of claim 29 wherein the polymer is conjugated to an RNA interference polynucleotide.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Mus musculus

<400> SEQUENCE: 1
gcaaaggcgu gccaacucat                                                 20

<210> SEQ ID NO 2
<211> LENGTH: 21
<212> TYPE: DNA
<213> ORGANISM: Mus musculus

<400> SEQUENCE: 2
```
tgaguuggca cgccuuugct t                                            21

<210> SEQ ID NO 3
<211> LENGTH: 21
<212> TYPE: DNA
<213> ORGANISM: Mus musculus

<400> SEQUENCE: 3
ggaucaucuc aagucuuact t                                            21

<210> SEQ ID NO 4
<211> LENGTH: 21
<212> TYPE: DNA
<213> ORGANISM: Mus musculus

<400> SEQUENCE: 4
guaagacuug agaugaucct t                                            21

<210> SEQ ID NO 5
<211> LENGTH: 24
<212> TYPE: DNA
<213> ORGANISM: Macaca fascicularis

<400> SEQUENCE: 5
uuagguuggu gaauggagcu cagt                                         24

<210> SEQ ID NO 6
<211> LENGTH: 21
<212> TYPE: DNA
<213> ORGANISM: Macaca fascicularis

<400> SEQUENCE: 6
cugagcucca uucaccaact t                                            21

<210> SEQ ID NO 7
<211> LENGTH: 21
<212> TYPE: DNA
<213> ORGANISM: Rattus norvegicus

<400> SEQUENCE: 7 ggaucuuau auuugaucca a                                             21

<210> SEQ ID NO 8
<211> LENGTH: 23
<212> TYPE: DNA
<213> ORGANISM: Rattus norvegicus

<400> SEQUENCE: 8
uuggaucaaa uauaagauuc ccu                                          23

<210> SEQ ID NO 9
<211> LENGTH: 23
<212> TYPE: DNA
<213> ORGANISM: Photinus pyralis

<400> SEQUENCE: 9
uaucuuacgc ugaguacuuc gat                                          23

```
<210> SEQ ID NO 10
<211> LENGTH: 21
<212> TYPE: DNA
<213> ORGANISM: Photinus pyralis

<400> SEQUENCE: 10
ucgaaguacu cagcguaagt t                                              21
```